US011318210B2

(12) United States Patent
Iacobelli et al.

(10) Patent No.: US 11,318,210 B2
(45) Date of Patent: May 3, 2022

(54) ENDOSIALIN-BINDING ANTIBODY

(71) Applicant: MEDIAPHARMA S.R.L., Chieti (IT)

(72) Inventors: Stefano Iacobelli, Rome (IT); Annalisa Di Risio, Chieti (IT); Enza Piccolo, Lanciano (IT); Gianluca Sala, Pescara (IT); Emily Capone, Cavallino (IT)

(73) Assignee: Fusion Pharmaceuticals Inc., Hamilton (CA)

( * ) Notice: Subject to any disclaimer, the term of this patent is extended or adjusted under 35 U.S.C. 154(b) by 59 days.

(21) Appl. No.: 16/075,849

(22) PCT Filed: Feb. 3, 2017

(86) PCT No.: PCT/EP2017/052399
§ 371 (c)(1),
(2) Date: Aug. 6, 2018

(87) PCT Pub. No.: WO2017/134234
PCT Pub. Date: Aug. 10, 2017

(65) Prior Publication Data
US 2019/0160180 A1 May 30, 2019

(30) Foreign Application Priority Data
Feb. 5, 2016 (EP) .................................. 16154507.4

(51) Int. Cl.
| | | |
|---|---|---|
| A61P 35/00 | (2006.01) | |
| C07K 16/18 | (2006.01) | |
| A61K 47/68 | (2017.01) | |
| C07K 16/28 | (2006.01) | |
| A61K 39/395 | (2006.01) | |
| A61K 49/00 | (2006.01) | |
| A61K 39/00 | (2006.01) | |

(52) U.S. Cl.
CPC ...... *A61K 47/6803* (2017.08); *A61K 39/3955* (2013.01); *A61K 47/6817* (2017.08); *A61K 49/0002* (2013.01); *A61P 35/00* (2018.01); *C07K 16/18* (2013.01); *C07K 16/2851* (2013.01); *A61K 2039/505* (2013.01); *A61K 2039/507* (2013.01); *C07K 2317/24* (2013.01); *C07K 2317/31* (2013.01); *C07K 2317/34* (2013.01); *C07K 2317/76* (2013.01); *C07K 2317/77* (2013.01)

(58) Field of Classification Search
CPC ............ A61K 47/6803; A61K 47/6817; C07K 16/18; C07K 16/2851; A61P 35/00
USPC ...................................................... 424/139.1
See application file for complete search history.

(56) References Cited

U.S. PATENT DOCUMENTS

| | | |
|---|---|---|
| 4,816,567 A | 3/1989 | Cabilly et al. |
| 2010/0260769 A1 | 10/2010 | Sass et al. |
| 2012/0328623 A1 | 12/2012 | Nobuaki |
| 2013/0260393 A1 | 10/2013 | O'Shannessy |

FOREIGN PATENT DOCUMENTS

| | | |
|---|---|---|
| EP | 0239400 A2 | 9/1987 |
| WO | 89/09622 A1 | 10/1989 |
| WO | 90/07861 A1 | 7/1990 |
| WO | 2006/0017759 | 2/2006 |
| WO | 2010/097825 | 9/2010 |

OTHER PUBLICATIONS

Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
Harmsen and Haard (Appl Microbiol Biotechnol 2007, 77:13-22).*
Rudikoff et al (Proc. Natl. Acad. Sci. USA. 1982; 79: 1979-1983).*
Bagley R G. "Endosialin: from vascular target to biomarker for human sarcomas." Biomark Med. Oct. 2009; 3(5):589-604.
Becker et al. "Tumor stroma marker endosialin (Tem1) is a binding partner of metastasis-related protein Mac-2 BP/90K." FASEB J Aug. 19, 2008; 22(8):3059-67.
Bergers et al. "Tumorigenesis and the angiogenic switch." Nat Rev Cancer. Jun. 2003; 3(6):401-10.
Brady et al. "Human endosialin (tumor endothelial marker 1) is abundantly expressed in highly malignant and invasive brain tumors." Journal of neuropathology and experimental neurology. 2004; 63(12):1274-1283.
Carson-Walter et al. "Characterization of TEM1/endosialin in human and murine brain tumors." BMC Cancer Nov. 30, 2009; 9:417.
Chambers et al. "Dissemination and growth of cancer cells in metastatic sites." Nat Rev Cancer. 2002; 2:563-72.

(Continued)

*Primary Examiner* — Yan Xiao
(74) *Attorney, Agent, or Firm* — Goodwin Procter LLP

(57) ABSTRACT

The present disclosure relates to the generation of an antibody that specifically recognizes and binds Endosialin, a cell surface antigen characteristic of tumor pericytes and cells of tumor stroma. The antibody has the ability to become internalized in Endosialin expressing cells and to block the activation of MAPK in PDGF stimulated human pericytes. The antibody is able to block angiogenesis induced by LGALS3BP, a known Endosialin interactor and to inhibit tumor growth alone and in combination with 1959, a humanized antibody against LGALS3BP in human osteosarcoma xenograft. Furthermore, upon conjugation of the humanized version of the anti-Endosialin antibody with a duocarmycin derivative, the resulting ADC displays potent and antigen dependent in vitro tumor cell cytotoxicity and effective antitumor efficacy in vivo. The disclosure is also related to nucleotides encoding the antibodies of the disclosure and cell expressing the antibodies.

24 Claims, 17 Drawing Sheets
Specification includes a Sequence Listing.

(56) References Cited

OTHER PUBLICATIONS

Christian et al. "Endosialin (Tem1) is a marker of tumor-associated myofibroblasts and tumor vessel-associated mural cells." The American journal of pathology. 2008; 172(2):486-494.
Christian et al. "Molecular cloning and characterization of endosialin, a C-type lectin-like cell surface receptor of tumor endothelium," J Biol Chem. Mar. 9, 2001; 276(10)7408-14.
Clackson et al. "Making antibody fragments using phage display libraries." Nature 1991; 15; 352(6336):624-8.
Cong et al. "Multiplex genome engineering using CRISPR/Cas systems." Science. 2013; 339:819-23.
Davies et al. "Levels of expression of endothelial markers specific to tumor-associated endothelial cells and their correlation with prognosis in patients with breast cancer." Clin Exp Metastasis. 2004; 21(1):31-37.
Hudson et al. "Engineered antibodies." Nat. Met. 2003; 9:129-134.
Jemal et al. "Cancer Statistics, 2009." CA Cancer J Clin 59. 2009: 225-49.
Jones et al., Replacing the complementarity-determining regions in a human antibody with those from a mouse, Nature, 1986, 321:522-525.
Kohler et al., Continuous cultures of fused cells secreting antibody of predefined specificity, Nature, 1975, 256:495-497.
MacFadyen et al. Endosialin "(TEM1, CD248) is a marker of stromal fibroblasts and is not selectively expressed on tumor endothelium." FEBS letters. 2005; 579(12):2569-2575.
Maia et al. "CD248 facilitates tumor growth via its cytoplasmic domain." BMC Cancer. May 8, 2011; 11:162.
Marty et al. "Isolation and characterization of a scFv antibody specific for tumor endothelial marker 1 (TEM1), a new reagent for targeted tumor therapy." Cancer Lett. 2006; 235:298-308.
Mehlen et al. "Metastasis: a question of life or death." Nat Rev Cancer. 2006; 6:449-58.
Peters et al. "Antibody-drug conjugates as novel anti-cancer chemotherapeutics." Biosci Rep, 2015. 35(4):1-20.
Piccolo et al. "LGALS3BP, lectin galactoside-binding soluble 3 binding protein, induces vascular endothelial growth factor in human breast cancer cells and promotes angiogenesis." J Mol Med (Berl). Jan. 2013; 91(1):83-94.
Reinicke. "Antibody epitope mapping using arrays of synthetic peptides." Methods Mol. Biol. 2004; 248:443-63.
Rettig et al. "Identification of endosialin, a cell surface glycoprotein of vascular endothelial cells in human cancer." Proc Natl Acad Sci USA. Nov. 15, 1992; 89(22): 10832-6.
Riechmann et al. "Reshaping human antibodies for therapy." Nature. 1988; 332:323-327.
Rouleau et al. "Endosialin expression inside populations in human sarcoma cell lines." Oncol Lett. Feb. 2012; 3(2):325-329.
Rouleau et al. "Endosialin is expressed in high grade and advanced sarcomas: evidence from clinical specimens and preclinical modeling." Int J Oncol Jul. 2011; 39(1):73-89.
Rouleau et al. "Endosialin: a novel malignant cell therapeutic target for neuroblastoma." Int J Oncol. Oct. 2011; 39(4):841.
Simonavicius et al. Endosialin (CD248) is a marker of tumor-associated pericytes in high-grade glioma. Mod Pathol. 2008;21:308-315.
Teicher B A. "Newer vascular targets: endosialin (review)." Int J Oncol. Feb. 2007; 30(2):305-12.
Thomas et al. "Antibody-drug conjugates for cancer therapy." Lancet Oncol, 2016. 17(6): p. e254-62.
Tomkowicz et al. "Endosialin/TEM-1/CD248 regulates pericyte proliferation through PDGF receptor signaling." Cancer Biol Ther. Jun. 1, 2010; 9(11):908-15.
Wang et al. "Identification of prostate specific membrane antigen (PSMA) as the target of monoclonal antibody 107-1A4 by proteinchip; array, surface-enhanced laser desorption/ionization (SELDI) technology." Int. J. Cancer, Jun. 15, 2001; 92 (6): 871-6.
Yang et al. "New molecular insights into osteosarcoma targeted therapy." Curr Opin Oncol. Jul. 2013; 25(4):398-406.
Rouleau, et al., "Anti-Endosialin Antibody-Drug Conjugate: Potential in Sarcoma and other Malignancies" Molecular Cancer Therapeutics, vol. 14, No. 9, Sep. 1, 2015.
Tomkowicz, et al., "Interaction of endosialin/TEM1 with extracellular matrix proteins mediates cell adhesion and migration", Proceedings of the National Academy of Sciences, National Academy of Sciences, US, vol. 104, No. 46, Nov. 13, 2007.
Rybinski, et al., "Targeting endosialin/CD248 through antibody-mediated internalization results in impaired pericyte maturation and dysfunctional tumor microvasculature" ONCOTARGET, vol. 6, No. 28 Jul. 4, 2015.
Kontsekova, et al., "Novel monoclonal antibodies specific for CTLD-SSC and sialomucin domains of endosialin, a mural cell marker of tumor vasculature", International Journal of Oncology, vol. 41, Jul. 23, 2012.
Zhao, et al., "Rapid isolation of high-affinity human antibodies against the tumor vascular marker Endosialin/TEM1, using a paired yeast-displayed/secretory scFv library platform", Journal of Immunological Methods, vol. 363, No. 2, Jan. 5, 2011.
International Search Report Issued in PCT/EP2017/052399.
AbyBiotech "Antibodies Overview." https://abybiotech.com/antibodies/overview; accessed Dec. 29, 2020.

\* cited by examiner

Target protein sequence (SEQ ID NO: 1)

MLLRLLLAWAAAGPTLGQDPWAAEPRAACGPSSCYALFPRRRTFLEAWRACRELGGDLATPRTPEEAQRVDSLVG
AGPASRLLWIGLQRQARQCQLQRPLRGFTWTTGDQDTAFTNWAQPASGGPCPAQRCVALEASGEHRWLEGSCTL
AVDGYLCQFGFEGACPALQDEAGQAGPAVYTTPFHLVSTEFEWLPFGSVAAVQCQAGRGASLLCVKQPEGGVGW
SRAGPLCLGTGCSPDNGGCEHECVEEVDGHVSCRCTEGFRLAADGRSCEDPCAQAPCEQQCEPGGPQGYSCHCRL
GFRPAEDDPHRCVDTDECQIAGVCQQMCVNYVGGFECYCSEGHELEADGISCSPAGAMGAQASQDLGDELLDDG
EDEEDEDEAWKAFNGGWTEMPGILWMEPTQPPDFALAYRPSFPEDREPQIPYPEPTWPPPLSAPRVPYHSSVLSV
TRPVVVSATHPTLPSAHQPPVIPATHPALSRDHQIPVIAANYPDLPSAYQPGILSVSHSAQPPAHQPPMISTKYPELF
PAHQSPMFPDTRVAGTQTTTHLPGIPPNHAPLVTTLGAQLPPQAPDALVLRTQATQLPIIPTAQPSLTTTSRSPVSPA
HQISVPAATQPAALPTLLPSQSPTNQTSPISPTHPHSKAPQIPREDGPSPKLALWLPSPAPTAAPTALGEAGLAEHSQ
RDDRWLLVALLVPTCVFLVVLLALGIVYCTRCGPHAPNKRITDCYRWVIHAGSKSPTEPMPPRGSLTGVQTCRTSV

B  Table 2. List of epitopes for antibody production (positions according to SEQ ID NO: 1)

| Start position | End position | Epitope sequences |
|---|---|---|
| 338 | 349 | SEGHELEADGIS (SEQ ID NO: 27) |
| 353 | 364 | AGAMGAQASQDL (SEQ ID NO: 28) |
| 398 | 409 | MEPTQPPDFALA (SEQ ID NO: 29) |
| 469 | 480 | IPATHPALSRDH (SEQ ID NO: 30) |
| 477 | 488 | SRDHQIPVIAAN (SEQ ID NO: 31) |
| 486 | 497 | AANYPDLPSAYQ (SEQ ID NO: 32) |
| 502 | 513 | SVSHSAQPPAHQ (SEQ ID NO: 33) |
| 546 | 557 | HLPGIPPNHAPL (SEQ ID NO: 34) |
| 555 | 566 | APLVTTLGAQLP (SEQ ID NO: 35) |
| 576 | 587 | RTQATQLPIIPT (SEQ ID NO: 36) |
| 601 | 612 | SPAHQISVPAAT (SEQ ID NO: 37) |
| 609 | 620 | PAATQPAALPTL (SEQ ID NO: 38) |
| 618 | 629 | PTLLPSQSPTNQ (SEQ ID NO: 39) |

Figure 8

I. VH humanisation
Original mouse sequence (SEQ ID NO: 8)
> IGHV2-6-7*02
QVQLQESGPGLVAPSQSLSITCTVSGFSLTGYGVNWVRQPPEKGLEWLGMIWVDGSTDYNSALKSRLNISK
DKSKSQVFLKMNSLQTDDTARYYCARGGYGAMDYWGQGTSVTVSS CDRs are underlined
Germ line mutations in red
o
Q as K in germ line
o
E as G in germ line
o
N as S in germ line humanized VH1 (SEQ ID NO: 18)
> IGHV4-4*08
QVQLQESGPGLVKPSETLSLTCTVSGFSLTGYGVNWIRQPPGKGLEWIGMIWVDGSTDYNSALKSRVTISVDTSKNQFSL
KLSSVTAADTAVYYCARGGYGAMDYWGQGTLVTVSS Mutations vs. original mouse sequence in blue Humanized VH2 (SEQ ID NO: 19)
> IGHV4-4*08 with germ line reversion
QVQLQESGPGLVKPSETLSLTCTVSGFSLTGYGVNWIRQPPEKGLEWIGMIWVDGSTDYNSALKSRVNISVDTSKNQFSL
KLSSVTAADTAVYYCARGGYGAMDYWGQGTLVTVSS
Humanized VH3 (SEQ ID NO: 20)
> IGHV4-61*05
QLQLQESGPGLVKPSETLSLTCTVSGFSLTGYGVNWIRQPPGKGLEWIGMIWVDGSTDYNSALKSRVTISVDKSKNQFSL
KLSSVTAADTAVYYCARGGYGAMDYWGQGTLVTVSS
Humanized VH4 (SEQ ID NO: 21)
> IGHV4-61*05 with germ line reversion
QLQLQESGPGLVKPSETLSLTCTVSGFSLTGYGVNWIRQPPEKGLEWIGMIWVDGSTDYNSALKSRVNISVDKSKNQFSL
KLSSVTAADTAVYYCARGGYGAMDYWGQGTLVTVSS II. VL humanisation
Original mouse sequence (SEQ ID NO: 9)
> IGKV15-103*01
DIQMNQSPSSLSASLGDTITITCHASQNINVWLTWYQQKPGNIPKLLIYKASNLHTGVPSRFSGSGSGTGFTLTISSLQP
EDIATYYCQQGQSYPWTFGGGTKLEIK
CDRs are underlined Humanized VL1 (SEQ ID NO: 22)
> IGKV1-12*01
DIQMTQSPSSVSASVGDRVTITCHASQNINVWLTWYQQKPGKAPKLLIYKASNLHTGVPSRFSGSGSGTDFTLTISSLQP
EDFATYYCQQGQSYPWTFGGGTKLEIK
Humanized VL2 (SEQ ID NO: 23)
> IGKV1-5*03
DIQMTQSPSTLSASVGDRVTITCHASQNINVWLTWYQQKPGKAPKLLIYKASNLHTGVPSRFSGSGSGTEFTLTISSLQP
DDFATYYCQQGQSYPWTFGGGTKLEIK
Humanized VL3 (SEQ ID NO: 24)
> IGKV1D-33*01
DIQMTQSPSSLSASVGDRVTITCHASQNINVWLTWYQQKPGKAPKLLIYKASNLHTGVPSRFSGSGSGTDFTFTISSLQP
EDIATYYCQQGQSYPWTFGGGTKLEIK
Humanized VL4 (SEQ ID NO: 25)
> IGKV1D-16*01
DIQMTQSPSSLSASVGDRVTITCHASQNINVWLTWYQQKPEKAPKSLIYKASNLHTGVPSRFSGSGSGTDFTLTISSLQP
EDFATYYCQQGQSYPWTFGGGTKLEIK Figure 9A
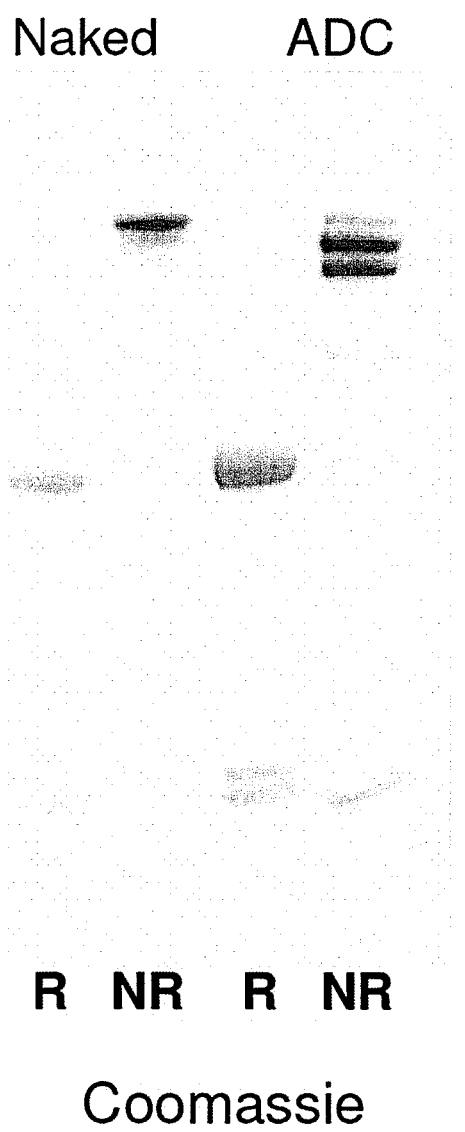
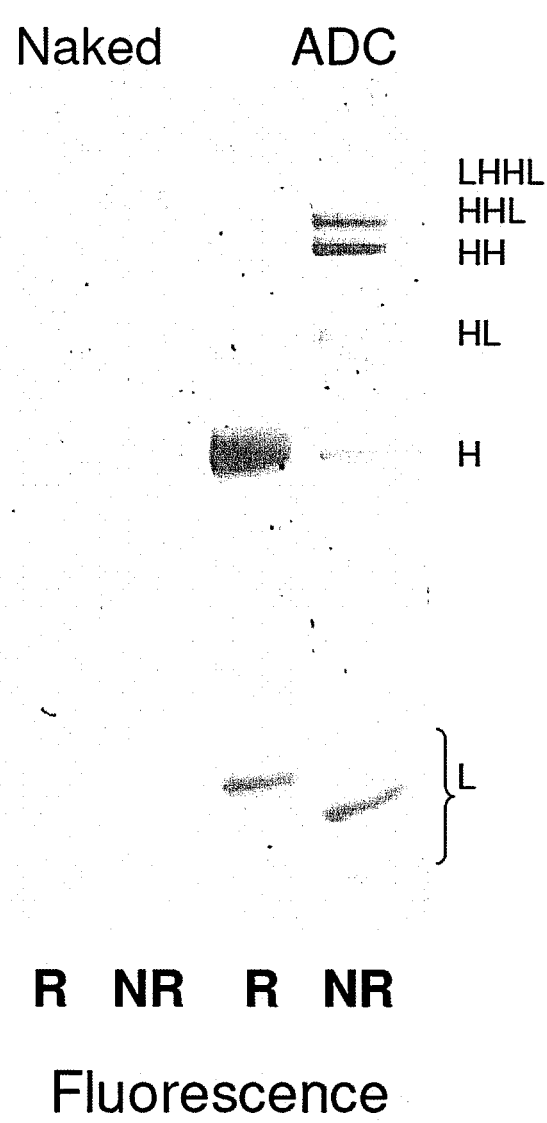

Figure 9B
SEC profile of the mAb
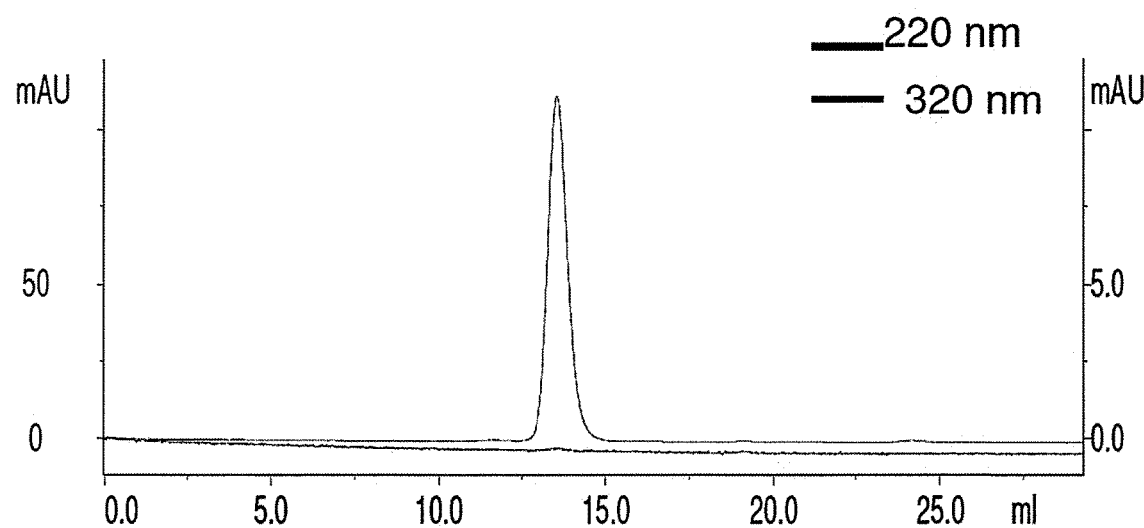
SEC profile of the ADC
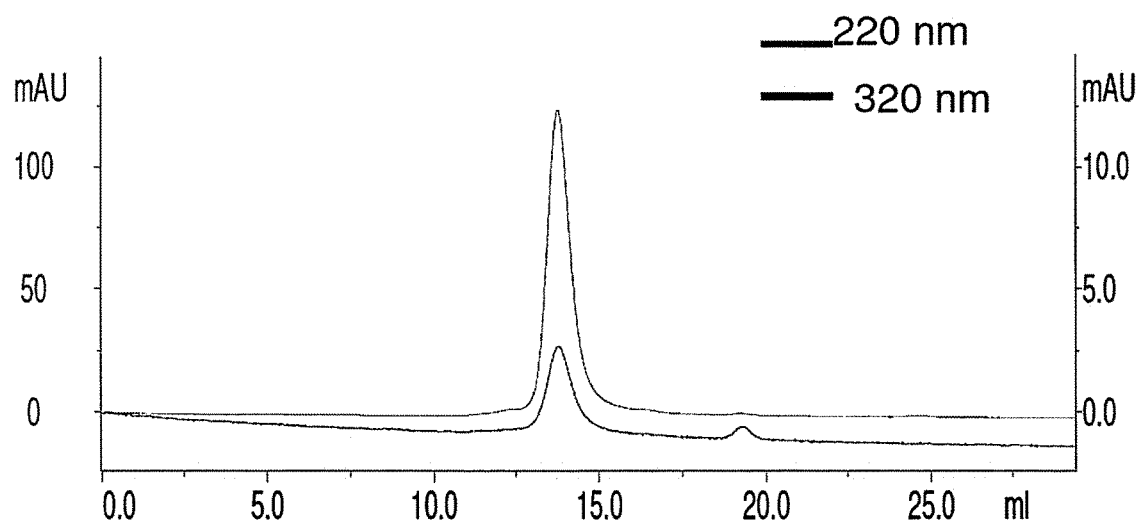

SEQUENCE LISTING

<160> NUMBER OF SEQ ID NOS: 40

<210> SEQ ID NO 1
<211> LENGTH: 757
<212> TYPE: PRT
<213> ORGANISM: Homo sapiens

<400> SEQUENCE: 1

```
Met Leu Leu Arg Leu Leu Leu Ala Trp Ala Ala Gly Pro Thr Leu
1               5                   10                  15

Gly Gln Asp Pro Trp Ala Ala Glu Pro Arg Ala Ala Cys Gly Pro Ser
                20                  25                  30

Ser Cys Tyr Ala Leu Phe Pro Arg Arg Arg Thr Phe Leu Glu Ala Trp
            35                  40                  45

Arg Ala Cys Arg Glu Leu Gly Gly Asp Leu Ala Thr Pro Arg Thr Pro
    50                  55                  60

Glu Glu Ala Gln Arg Val Asp Ser Leu Val Gly Ala Gly Pro Ala Ser
65                  70                  75                  80

Arg Leu Leu Trp Ile Gly Leu Gln Arg Gln Ala Arg Gln Cys Gln Leu
                85                  90                  95

Gln Arg Pro Leu Arg Gly Phe Thr Trp Thr Thr Gly Asp Gln Asp Thr
                100                 105                 110

Ala Phe Thr Asn Trp Ala Gln Pro Ala Ser Gly Gly Pro Cys Pro Ala
            115                 120                 125

Gln Arg Cys Val Ala Leu Glu Ala Ser Gly Glu His Arg Trp Leu Glu
    130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Gln Asp Glu Ala Gly Gln Ala Gly Pro
                165                 170                 175

Ala Val Tyr Thr Thr Pro Phe His Leu Val Ser Thr Glu Phe Glu Trp
                180                 185                 190

Leu Pro Phe Gly Ser Val Ala Ala Val Gln Cys Gln Ala Gly Arg Gly
                195                 200                 205

Ala Ser Leu Leu Cys Val Lys Gln Pro Glu Gly Gly Val Gly Trp Ser
    210                 215                 220

Arg Ala Gly Pro Leu Cys Leu Gly Thr Gly Cys Ser Pro Asp Asn Gly
225                 230                 235                 240

Gly Cys Glu His Glu Cys Val Glu Glu Val Asp Gly His Val Ser Cys
                245                 250                 255

Arg Cys Thr Glu Gly Phe Arg Leu Ala Ala Asp Gly Arg Ser Cys Glu
                260                 265                 270

Asp Pro Cys Ala Gln Ala Pro Cys Glu Gln Cys Glu Pro Gly Gly
            275                 280                 285

Pro Gln Gly Tyr Ser Cys His Cys Arg Leu Gly Phe Arg Pro Ala Glu
    290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
                340                 345                 350

Ala Gly Ala Met Gly Ala Gln Ala Ser Gln Asp Leu Gly Asp Glu Leu
            355                 360                 365
```

Leu Asp Asp Gly Glu Asp Glu Glu Asp Glu Asp Ala Trp Lys Ala
370                 375                 380

Phe Asn Gly Gly Trp Thr Glu Met Pro Gly Ile Leu Trp Met Glu Pro
385                 390                 395                 400

Thr Gln Pro Pro Asp Phe Ala Leu Ala Tyr Arg Pro Ser Phe Pro Glu
            405                 410                 415

Asp Arg Glu Pro Gln Ile Pro Tyr Pro Glu Pro Thr Trp Pro Pro Pro
            420                 425                 430

Leu Ser Ala Pro Arg Val Pro Tyr His Ser Ser Val Leu Ser Val Thr
            435                 440                 445

Arg Pro Val Val Val Ser Ala Thr His Pro Thr Leu Pro Ser Ala His
450                 455                 460

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
                485                 490                 495

Gln Pro Gly Ile Leu Ser Val Ser His Ser Ala Gln Pro Pro Ala His
                500                 505                 510

Gln Pro Pro Met Ile Ser Thr Lys Tyr Pro Glu Leu Phe Pro Ala His
            515                 520                 525

Gln Ser Pro Met Phe Pro Asp Thr Arg Val Ala Gly Thr Gln Thr Thr
530                 535                 540

Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                565                 570                 575

Thr Gln Ala Thr Gln Leu Pro Ile Ile Pro Thr Ala Gln Pro Ser Leu
            580                 585                 590

Thr Thr Thr Ser Arg Ser Pro Val Ser Pro Ala His Gln Ile Ser Val
            595                 600                 605

Pro Ala Ala Thr Gln Pro Ala Ala Leu Pro Thr Leu Leu Pro Ser Gln
610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                645                 650                 655

Leu Trp Leu Pro Ser Pro Ala Pro Thr Ala Ala Pro Thr Ala Leu Gly
            660                 665                 670

Glu Ala Gly Leu Ala Glu His Ser Gln Arg Asp Asp Arg Trp Leu Leu
            675                 680                 685

Val Ala Leu Leu Val Pro Thr Cys Val Phe Leu Val Val Leu Leu Ala
690                 695                 700

Leu Gly Ile Val Tyr Cys Thr Arg Cys Gly Pro His Ala Pro Asn Lys
705                 710                 715                 720

Arg Ile Thr Asp Cys Tyr Arg Trp Val Ile His Ala Gly Ser Lys Ser
                725                 730                 735

Pro Thr Glu Pro Met Pro Pro Arg Gly Ser Leu Thr Gly Val Gln Thr
            740                 745                 750

Cys Arg Thr Ser Val
            755

<210> SEQ ID NO 2
<211> LENGTH: 5
<212> TYPE: PRT

```
<213> ORGANISM: artificial
<220> FEATURE:
<223> OTHER INFORMATION: CDR-H1

<400> SEQUENCE: 2

Gly Tyr Gly Val Asn
1               5

<210> SEQ ID NO 3
<211> LENGTH: 16
<212> TYPE: PRT
<213> ORGANISM: artificial
<220> FEATURE:
<223> OTHER INFORMATION: CDR-H2

<400> SEQUENCE: 3

Met Ile Trp Val Asp Gly Ser Thr Asp Tyr Asn Ser Ala Leu Lys Ser
1               5                  10                  15

<210> SEQ ID NO 4
<211> LENGTH: 8
<212> TYPE: PRT
<213> ORGANISM: artificial
<220> FEATURE:
<223> OTHER INFORMATION: CDR-H3

<400> SEQUENCE: 4

Gly Gly Tyr Gly Ala Met Asp Tyr
1               5

<210> SEQ ID NO 5
<211> LENGTH: 11
<212> TYPE: PRT
<213> ORGANISM: artificial
<220> FEATURE:
<223> OTHER INFORMATION: CDR-L1

<400> SEQUENCE: 5

His Ala Ser Gln Asn Ile Asn Val Trp Leu Thr
1               5                   10

<210> SEQ ID NO 6
<211> LENGTH: 7
<212> TYPE: PRT
<213> ORGANISM: artificial
<220> FEATURE:
<223> OTHER INFORMATION: CDR-L2

<400> SEQUENCE: 6

Lys Ala Ser Asn Leu His Thr
1               5

<210> SEQ ID NO 7
<211> LENGTH: 9
<212> TYPE: PRT
<213> ORGANISM: artificial
<220> FEATURE:
<223> OTHER INFORMATION: CDR_L3

<400> SEQUENCE: 7

Gln Gln Gly Gln Ser Tyr Pro Trp Thr
1               5

<210> SEQ ID NO 8
<211> LENGTH: 116
<212> TYPE: PRT
<213> ORGANISM: artificial
```

```
<220> FEATURE:
<223> OTHER INFORMATION: vH
<220> FEATURE:
<221> NAME/KEY: MISC_FEATURE
<222> LOCATION: (1)..(30)
<223> OTHER INFORMATION: HFR-1
<220> FEATURE:
<221> NAME/KEY: MISC_FEATURE
<222> LOCATION: (26)..(35)
<223> OTHER INFORMATION: CDR-H1 (alternative)
<220> FEATURE:
<221> NAME/KEY: MISC_FEATURE
<222> LOCATION: (31)..(35)
<223> OTHER INFORMATION: CDR-H1
<220> FEATURE:
<221> NAME/KEY: MISC_FEATURE
<222> LOCATION: (36)..(49)
<223> OTHER INFORMATION: HFR-2
<220> FEATURE:
<221> NAME/KEY: MISC_FEATURE
<222> LOCATION: (50)..(65)
<223> OTHER INFORMATION: CDR-H2
<220> FEATURE:
<221> NAME/KEY: MISC_FEATURE
<222> LOCATION: (66)..(97)
<223> OTHER INFORMATION: HFR-3
<220> FEATURE:
<221> NAME/KEY: MISC_FEATURE
<222> LOCATION: (98)..(105)
<223> OTHER INFORMATION: CDR-H3
<220> FEATURE:
<221> NAME/KEY: MISC_FEATURE
<222> LOCATION: (106)..(116)
<223> OTHER INFORMATION: HFR-4

<400> SEQUENCE: 8

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Glu Lys Gly Leu Glu Trp Leu
        35                  40                  45

Gly Met Ile Trp Val Asp Gly Ser Thr Asp Tyr Asn Ser Ala Leu Lys
    50                  55                  60

Ser Arg Leu Asn Ile Ser Lys Asp Lys Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly Gly Tyr Gly Ala Met Asp Tyr Trp Gly Gln Gly Thr Ser Val
            100                 105                 110

Thr Val Ser Ser
        115

<210> SEQ ID NO 9
<211> LENGTH: 107
<212> TYPE: PRT
<213> ORGANISM: artificial
<220> FEATURE:
<223> OTHER INFORMATION: vL
<220> FEATURE:
<221> NAME/KEY: MISC_FEATURE
<222> LOCATION: (1)..(23)
<223> OTHER INFORMATION: LFR-1
<220> FEATURE:
<221> NAME/KEY: MISC_FEATURE
<222> LOCATION: (24)..(34)
<223> OTHER INFORMATION: CDR-L2
<220> FEATURE:
<221> NAME/KEY: MISC_FEATURE
<222> LOCATION: (35)..(49)
```

```
<223> OTHER INFORMATION: LFR-2
<220> FEATURE:
<221> NAME/KEY: MISC_FEATURE
<222> LOCATION: (50)..(56)
<223> OTHER INFORMATION: CDR-L2
<220> FEATURE:
<221> NAME/KEY: MISC_FEATURE
<222> LOCATION: (57)..(88)
<223> OTHER INFORMATION: LFR-3
<220> FEATURE:
<221> NAME/KEY: MISC_FEATURE
<222> LOCATION: (89)..(97)
<223> OTHER INFORMATION: CDR-L3
<220> FEATURE:
<221> NAME/KEY: MISC_FEATURE
<222> LOCATION: (98)..(107)
<223> OTHER INFORMATION: LFR-4

<400> SEQUENCE: 9

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Thr Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105

<210> SEQ ID NO 10
<211> LENGTH: 135
<212> TYPE: PRT
<213> ORGANISM: artificial
<220> FEATURE:
<223> OTHER INFORMATION: heavy chain
<220> FEATURE:
<221> NAME/KEY: MISC_FEATURE
<222> LOCATION: (20)..(135)
<223> OTHER INFORMATION: vH

<400> SEQUENCE: 10

Met Ala Val Leu Ala Leu Leu Phe Cys Leu Val Thr Phe Pro Ser Cys
1               5                   10                  15

Ile Leu Ser Gln Val Gln Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Gly Tyr Gly Val Asn Trp Val Arg Gln Pro Pro Glu Lys Gly Leu
50                  55                  60

Glu Trp Leu Gly Met Ile Trp Val Asp Gly Ser Thr Asp Tyr Asn Ser
65                  70                  75                  80

Ala Leu Lys Ser Arg Leu Asn Ile Ser Lys Asp Lys Ser Lys Ser Gln
                85                  90                  95

Val Phe Leu Lys Met Asn Ser Leu Gln Thr Asp Asp Thr Ala Arg Tyr
            100                 105                 110

Tyr Cys Ala Arg Gly Gly Tyr Gly Ala Met Asp Tyr Trp Gly Gln Gly
        115                 120                 125
```

Thr Ser Val Thr Val Ser Ser
    130             135

<210> SEQ ID NO 11
<211> LENGTH: 135
<212> TYPE: PRT
<213> ORGANISM: artificial
<220> FEATURE:
<223> OTHER INFORMATION: heavy chain
<220> FEATURE:
<221> NAME/KEY: MISC_FEATURE
<222> LOCATION: (20)..(135)
<223> OTHER INFORMATION: vH

<400> SEQUENCE: 11

Met Asn Phe Gly Leu Arg Leu Ile Phe Leu Val Leu Thr Leu Lys Gly
1               5                   10                  15

Val Gln Cys Gln Val Gln Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Gly Tyr Gly Val Asn Trp Val Arg Gln Pro Pro Glu Lys Gly Leu
    50                  55                  60

Glu Trp Leu Gly Met Ile Trp Val Asp Gly Ser Thr Asp Tyr Asn Ser
65                  70                  75                  80

Ala Leu Lys Ser Arg Leu Asn Ile Ser Lys Asp Lys Ser Lys Ser Gln
                85                  90                  95

Val Phe Leu Lys Met Asn Ser Leu Gln Thr Asp Asp Thr Ala Arg Tyr
            100                 105                 110

Tyr Cys Ala Arg Gly Gly Tyr Gly Ala Met Asp Tyr Trp Gly Gln Gly
        115                 120                 125

Thr Ser Val Thr Val Ser Ser
    130             135

<210> SEQ ID NO 12
<211> LENGTH: 127
<212> TYPE: PRT
<213> ORGANISM: artificial
<220> FEATURE:
<223> OTHER INFORMATION: light chain
<220> FEATURE:
<221> NAME/KEY: MISC_FEATURE
<222> LOCATION: (21)..(127)
<223> OTHER INFORMATION: vL

<400> SEQUENCE: 12

Met Arg Val Leu Ala Glu Leu Leu Gly Leu Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys His Ala Ser Gln Asn
        35                  40                  45

Ile Asn Val Trp Leu Thr Trp Tyr Gln Gln Lys Pro Gly Asn Ile Pro
    50                  55                  60

Lys Leu Leu Ile Tyr Lys Ala Ser Asn Leu His Thr Gly Val Pro Ser
65                  70                  75                  80

Arg Phe Ser Gly Ser Gly Ser Gly Thr Gly Phe Thr Leu Thr Ile Ser
                85                  90                  95

Ser Leu Gln Pro Glu Asp Ile Ala Thr Tyr Tyr Cys Gln Gln Gly Gln
            100                 105                 110

Ser Tyr Pro Trp Thr Phe Gly Gly Gly Thr Lys Leu Glu Ile Lys
        115                 120                 125

<210> SEQ ID NO 13
<211> LENGTH: 126
<212> TYPE: PRT
<213> ORGANISM: artificial
<220> FEATURE:
<223> OTHER INFORMATION: light chain
<220> FEATURE:
<221> NAME/KEY: MISC_FEATURE
<222> LOCATION: (20)..(126)
<223> OTHER INFORMATION: vL

<400> SEQUENCE: 13

Met Asn Phe Gly Leu Arg Leu Ile Phe Leu Val Leu Thr Leu Lys Gly
1               5                   10                  15

Val Gln Cys Asp Ile Gln Met Asn Gln Ser Pro Ser Ser Leu Ser Ala
            20                  25                  30

Ser Leu Gly Asp Thr Ile Thr Ile Thr Cys His Ala Ser Gln Asn Ile
        35                  40                  45

Asn Val Trp Leu Thr Trp Tyr Gln Gln Lys Pro Gly Asn Ile Pro Lys
    50                  55                  60

Leu Leu Ile Tyr Lys Ala Ser Asn Leu His Thr Gly Val Pro Ser Arg
65                  70                  75                  80

Phe Ser Gly Ser Gly Ser Gly Thr Gly Phe Thr Leu Thr Ile Ser Ser
                85                  90                  95

Leu Gln Pro Glu Asp Ile Ala Thr Tyr Tyr Cys Gln Gln Gly Gln Ser
            100                 105                 110

Tyr Pro Trp Thr Phe Gly Gly Gly Thr Lys Leu Glu Ile Lys
        115                 120                 125

<210> SEQ ID NO 14
<211> LENGTH: 405
<212> TYPE: DNA
<213> ORGANISM: artificial
<220> FEATURE:
<223> OTHER INFORMATION: heavy chain

<400> SEQUENCE: 14
atggctgtcc tggcattact cttctgcctg gtaacattcc caagctgtat cctttcccag      60
gtgcagctgc aggagtcagg acctggcctg gtggcgccct cacagagcct gtccatcaca     120
tgcaccgtct cagggttctc attaaccggc tatggtgtaa actgggttcg ccagcctcca     180
gaaaagggtc tggagtggct gggaatgata tgggttgatg aagcacaga ctataattca      240 gctctcaaat ccagactgaa catcagcaag acaagtcca agagccaagt tttcttaaaa      300
atgaacagtc tgcaaactga tgacacagcc aggtactact gtgccagagg gggctacggt     360
gctatggact actggggtca aggaacctca gtcaccgtct cctca                     405

<210> SEQ ID NO 15
<211> LENGTH: 1419
<212> TYPE: DNA
<213> ORGANISM: artificial
<220> FEATURE:
<223> OTHER INFORMATION: heavy chain

<400> SEQUENCE: 15
gcggccgcca tgaattttgg actgaggctg attttcctgg tgctgaccct gaaaggcgtc      60
cagtgtcagg tccagctgca ggagtcaggt cccggcctgg tggcaccatc ccagagcctg     120

| | |
|---|---|
| tctatcacct gcacggtctc cggcttcagc ctgacaggct acggagtgaa ctgggtcaga | 180 |
| cagcccctg agaaagggct ggaatggctg gtatgatct gggtggacgg aagcaccgat | 240 |
| tataactctg ccctgaaaag taggctgaat atttccaagg ataagtcgaa gtcacaggtc | 300 |
| tttctgaaga tgaactccct gcagactgac gataccgccc ggtactattg tgctagggg | 360 |
| gggtatggtg ctatggatta ttggggacag gggacaagcg tcacagtctc gagcgctagc | 420 |
| acaaagggcc ctagtgtgtt tcctctggct ccctcttcca atccacttc tggtggcact | 480 |
| gctgctctgg gatgcctggt gaaggattac tttcctgaac ctgtgactgt ctcatggaac | 540 |
| tctggtgctc tgacttctgg tgtccacact ttccctgctg tgctgcagtc tagtggactg | 600 |
| tactctctgt catctgtggt cactgtgccc tcttcatctc tgggaaccca gacctacatt | 660 |
| tgtaatgtga accacaaacc atccaacact aaagtggaca aaaagtgga acccaaatcc | 720 |
| tgtgacaaaa cccacacctg cccaccttgt cctgcccctg aactgctggg aggaccttct | 780 |
| gtgtttctgt tccccccaa accaaaggat accctgatga tctctagaac ccctgaggtg | 840 |
| acatgtgtgg tggtggatgt gtctcatgag accctgaggt caaattcaa ctggtacgtg | 900 |
| gatggagtgg aagtccacaa tgccaaaacc aagcctagag aggaacagta caattcaacc | 960 |
| tacagagtgg tcagtgtgct gactgtgctg catcaggatt ggctgaatgg caaggaatac | 1020 |
| aagtgtaaag tctcaaacaa ggccctgcct gctccaattg agaaaacaat ctcaaaggcc | 1080 |
| aagggacagc ctagggaacc ccaggtctac accctgccac cttcaagaga ggaaatgacc | 1140 |
| aaaaaccagg tgtccctgac atgcctggtc aaaggcttct acccttctga cattgctgtg | 1200 |
| gagtgggagt caaatggaca gcctgagaac aactacaaaa caacccccc tgtgctggat | 1260 |
| tctgatggct ctttcttct gtactccaaa ctgactgtgg acaagtctag atggcagcag | 1320 |
| gggaatgtct ttcttgctc tgtcatgcat gaggctctgc ataaccacta cactcagaaa | 1380 |
| tccctgtctc tgtctcccgg gaaatgatag taaaagctt | 1419 |

<210> SEQ ID NO 16
<211> LENGTH: 381
<212> TYPE: DNA
<213> ORGANISM: artificial
<220> FEATURE:
<223> OTHER INFORMATION: light chain

<400> SEQUENCE: 16

| | |
|---|---|
| atgagggtcc ttgctgagct cctggggctg ctgctgttct gcttttagg tgtgagatgt | 60 |
| gacatccaga tgaaccagtc tccatccagt ctgtctgcat cccttggaga cacaattacc | 120 |
| atcacttgcc atgccagtca gaacattaat gtttggttaa cctggtacca gcagaaacca | 180 |
| ggaaatattc ctaaactatt gatctataag gcttccaact tgcacacagg cgtcccatca | 240 |
| aggtttagtg gcagtggatc tggaacaggt ttcacattaa ccatcagcag cctgcagcct | 300 |
| gaagacattg ccacttacta ctgtcaacag ggtcaaagtt atccgtggac gttcggtgga | 360 |
| ggcaccaagc tggaaatcaa a | 381 |

<210> SEQ ID NO 17
<211> LENGTH: 723
<212> TYPE: DNA
<213> ORGANISM: artificial
<220> FEATURE:
<223> OTHER INFORMATION: light chain

<400> SEQUENCE: 17

| | |
|---|---|
| gcggccgcca tgaattttgg actgaggctg attttcctgg tgctgaccct gaaaggcgtc | 60 |

```
cagtgtgaca ttcagatgaa tcagtctcct tcctctctga gtgcctcact gggcgacacc    120
atcacaatta cttgccacgc ttcccagaac atcaatgtgt ggctgacatg gtatcagcag    180
aagcctggca acatccctaa gctgctgatc tacaaagcat caaatctgca tactggagtc    240
ccaagcaggt tctccggcag cggatctggg accggtttta ccctgacaat ctccagcctg    300
cagcccgagg atattgccac ctactattgt cagcaggggc agagctatcc ttggaccttc    360 ggggcggca ctaaactgga aatcaaacgt acggtcgcgg cgccttctgt gttcattttc    420
cccccatctg atgaacagct gaaatctggc actgcttctg tggtctgtct gctgaacaac    480
ttctacccta gagaggccaa agtccagtgg aaagtggaca atgctctgca gagtgggaat    540
tcccaggaat ctgtcactga gcaggactct aaggatagca catactccct gtcctctact    600
ctgacactga gcaaggctga ttacgagaaa cacaaagtgt acgcctgtga agtcacacat    660
caggggctgt ctagtcctgt gaccaaatcc ttcaataggg gagagtgctg atagtaaaag    720
ctt                                                                  723
```

```
<210> SEQ ID NO 18
<211> LENGTH: 116
<212> TYPE: PRT
<213> ORGANISM: Artificial Sequence
<220> FEATURE:
<223> OTHER INFORMATION: Humanized VH1 (IGHV4-4*08)

<400> SEQUENCE: 18

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Ile
        35                  40                  45

Gly Met Ile Trp Val Asp Gly Ser Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Gly Ala Met Asp Tyr Trp Gly Gln Gly Thr Leu Val
               100                 105                 110

Thr Val Ser Ser
        115
```

```
<210> SEQ ID NO 19
<211> LENGTH: 116
<212> TYPE: PRT
<213> ORGANISM: Artificial Sequence
<220> FEATURE:
<223> OTHER INFORMATION: Humanized VH2 (IGHV4-4*08 with germ line
      reversion)

<400> SEQUENCE: 19

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Glu Lys Gly Leu Glu Trp Ile
        35                  40                  45
```

```
Gly Met Ile Trp Val Asp Gly Ser Thr Asp Tyr Asn Ser Ala Leu Lys
    50                  55                  60

Ser Arg Val Asn Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Gly Ala Met Asp Tyr Trp Gly Gln Gly Thr Leu Val
            100                 105                 110

Thr Val Ser Ser
        115

<210> SEQ ID NO 20
<211> LENGTH: 116
<212> TYPE: PRT
<213> ORGANISM: Artificial Sequence
<220> FEATURE:
<223> OTHER INFORMATION: Humanized VH3 (IGHV4-61*05)

<400> SEQUENCE: 20

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Lys Gly Leu Glu Trp Ile
        35                  40                  45

Gly Met Ile Trp Val Asp Gly Ser Thr Asp Tyr Asn Ser Ala Leu Lys
    50                  55                  60

Ser Arg Val Thr Ile Ser Val Asp Lys Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Gly Ala Met Asp Tyr Trp Gly Gln Gly Thr Leu Val
            100                 105                 110

Thr Val Ser Ser
        115

<210> SEQ ID NO 21
<211> LENGTH: 116
<212> TYPE: PRT
<213> ORGANISM: Artificial Sequence
<220> FEATURE:
<223> OTHER INFORMATION: Humanized VH4 (IGHV4-61*05 with germ line
      reversion)

<400> SEQUENCE: 21

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Gly Tyr
            20                  25                  30

Gly Val Asn Trp Ile Arg Gln Pro Pro Gly Glu Lys Gly Leu Glu Trp Ile
        35                  40                  45

Gly Met Ile Trp Val Asp Gly Ser Thr Asp Tyr Asn Ser Ala Leu Lys
    50                  55                  60

Ser Arg Val Asn Ile Ser Val Asp Lys Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Gly Ala Met Asp Tyr Trp Gly Gln Gly Thr Leu Val
```

```
                100             105             110
Thr Val Ser Ser
            115

<210> SEQ ID NO 22
<211> LENGTH: 107
<212> TYPE: PRT
<213> ORGANISM: Artificial Sequence
<220> FEATURE:
<223> OTHER INFORMATION: Humanized VL1 (IGKV1-12*01)

<400> SEQUENCE: 22

Asp Ile Gln Met Thr Gln Ser Pro Ser Ser Val Ser Ala Ser Val Gly
1               5                   10                  15

Asp Arg Val Thr Ile Thr Cys His Ala Ser Gln Asn Ile Asn Val Trp
            20                  25                  30

Leu Thr Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Humanized VL2 (IGKV1-5*03)

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys His Ala Ser Gln Asn Ile Asn Val Trp
            20                  25                  30

Leu Thr Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Humanized VL3 (IGKV1D-33*01)

<400> SEQUENCE: 24

Asp Ile Gln Met Thr Gln Ser Pro Ser Ser Leu Ser Ala Ser Val Gly
1               5                   10                  15
```

```
Asp Arg Val Thr Ile Thr Cys His Ala Ser Gln Asn Ile Asn Val Trp
            20                  25                  30

Leu Thr Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105

<210> SEQ ID NO 25
<211> LENGTH: 107
<212> TYPE: PRT
<213> ORGANISM: Artificial Sequence
<220> FEATURE:
<223> OTHER INFORMATION: Humanized VL4 (IGKVD-16*01)

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Asn Val Trp
            20                  25                  30

Leu Thr Trp Tyr Gln Gln Lys Pro Glu Lys Ala Pro Lys Ser Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105

<210> SEQ ID NO 26
<211> LENGTH: 10
<212> TYPE: PRT
<213> ORGANISM: Artificial Sequence
<220> FEATURE:
<223> OTHER INFORMATION: CDR-H1 (alternative)

<400> SEQUENCE: 26

Gly Phe Ser Leu Thr Gly Tyr Gly Val Asn
1               5                   10

<210> SEQ ID NO 27
<211> LENGTH: 12
<212> TYPE: PRT
<213> ORGANISM: Homo sapiens

<400> SEQUENCE: 27

Ser Glu Gly His Glu Leu Glu Ala Asp Gly Ile Ser
1               5                   10

<210> SEQ ID NO 28
<211> LENGTH: 12
<212> TYPE: PRT
<213> ORGANISM: Homo sapiens
```

<400> SEQUENCE: 28

Ala Gly Ala Met Gly Ala Gln Ala Ser Gln Asp Leu
1               5                   10

<210> SEQ ID NO 29
<211> LENGTH: 12
<212> TYPE: PRT
<213> ORGANISM: Homo sapiens

<400> SEQUENCE: 29

Met Glu Pro Thr Gln Pro Pro Asp Phe Ala Leu Ala
1               5                   10

<210> SEQ ID NO 30
<211> LENGTH: 12
<212> TYPE: PRT
<213> ORGANISM: Homo sapiens

<400> SEQUENCE: 30

Ile Pro Ala Thr His Pro Ala Leu Ser Arg Asp His
1               5                   10

<210> SEQ ID NO 31
<211> LENGTH: 12
<212> TYPE: PRT
<213> ORGANISM: Homo sapiens

<400> SEQUENCE: 31

Ser Arg Asp His Gln Ile Pro Val Ile Ala Ala Asn
1               5                   10

<210> SEQ ID NO 32
<211> LENGTH: 12
<212> TYPE: PRT
<213> ORGANISM: Homo sapiens

<400> SEQUENCE: 32

Ala Ala Asn Tyr Pro Asp Leu Pro Ser Ala Tyr Gln
1               5                   10

<210> SEQ ID NO 33
<211> LENGTH: 12
<212> TYPE: PRT
<213> ORGANISM: Homo sapiens

<400> SEQUENCE: 33

Ser Val Ser His Ser Ala Gln Pro Pro Ala His Gln
1               5                   10

<210> SEQ ID NO 34
<211> LENGTH: 12
<212> TYPE: PRT
<213> ORGANISM: Homo sapiens

<400> SEQUENCE: 34

His Leu Pro Gly Ile Pro Pro Asn His Ala Pro Leu
1               5                   10

<210> SEQ ID NO 35
<211> LENGTH: 12
<212> TYPE: PRT
<213> ORGANISM: Homo sapiens

<400> SEQUENCE: 35

```
Ala Pro Leu Val Thr Thr Leu Gly Ala Gln Leu Pro
1               5                   10

<210> SEQ ID NO 36
<211> LENGTH: 12
<212> TYPE: PRT
<213> ORGANISM: Homo sapiens

<400> SEQUENCE: 36

Arg Thr Gln Ala Thr Gln Leu Pro Ile Ile Pro Thr
1               5                   10

<210> SEQ ID NO 37
<211> LENGTH: 12
<212> TYPE: PRT
<213> ORGANISM: Homo sapiens

<400> SEQUENCE: 37

Ser Pro Ala His Gln Ile Ser Val Pro Ala Ala Thr
1               5                   10

<210> SEQ ID NO 38
<211> LENGTH: 12
<212> TYPE: PRT
<213> ORGANISM: Homo sapiens

<400> SEQUENCE: 38

Pro Ala Ala Thr Gln Pro Ala Ala Leu Pro Thr Leu
1               5                   10

<210> SEQ ID NO 39
<211> LENGTH: 12
<212> TYPE: PRT
<213> ORGANISM: Homo sapiens

<400> SEQUENCE: 39

Pro Thr Leu Leu Pro Ser Gln Ser Pro Thr Asn Gln
1               5                   10

<210> SEQ ID NO 40
<211> LENGTH: 12
<212> TYPE: PRT
<213> ORGANISM: Homo sapiens

<400> SEQUENCE: 40

Pro His Ser Lys Ala Pro Gln Ile Pro Arg Glu Asp
1               5                   10
```

ENDOSIALIN-BINDING ANTIBODY

CROSS REFERENCE TO RELATED APPLICATIONS

This application is the National Stage of International Application No. PCT/EP2017/052399, filed Feb. 3, 2017, which claims the benefit of European Application No. 16154507.4, filed Feb. 5, 2016. The contents of both applications are hereby incorporated by reference in their entirety.

The present invention relates to the development of a murine, chimeric (mouse/human) and humanized antibodies that specifically bind to Endosialin, a cell surface antigen characteristic of tumor pericytes and cells of tumor stroma. The antibody has the ability to become internalized in Endosialin expressing cells and to block the activation of MAPK in PDGF stimulated human pericytes. The antibody is able to block angiogenesis induced by LGALS3BP, a known Endosialin interactor and to inhibit growth of human sarcoma xenografts. The in vivo growth inhibitory effect is potentiated when the antibody is administered in combination with 1959, a humanized monoclonal antibody against LGALS3BP.

The invention is also related to the development of an Antibody-Drug Conjugate (ADC) based on a humanized monoclonal antibody specifically binding Endosialin coupled to a payload consisting of a duocarmycin derivative by means of a cleavable linker.

Finally, the invention is related to nucleotides encoding the antibodies of the invention and to cells expressing the antibodies.

DESCRIPTION

The present invention relates to an antibody, particularly a monoclonal antibody, which binds to the tumor endothelial marker Endosialin (also known also as TEM-1 and CD248), wherein said binding induces antibody internalization and reduces MAPK activation in PDGF stimulated human pericytes, and compositions comprising such an antibody as well as methods using such an antibody.

Cancer is a disease characterized by a series of somatic changes affecting the structure and/or expression of oncogenes and tumor suppressor genes. It is well known that tumor growth beyond diameters of 1-2 mm depends on formation of new blood vessels, a process known as angiogenesis, as well as on transformation of stromal fibroblasts and extracellular matrix proteins[1]. In vitro and in vivo studies have demonstrated that tumor stroma and vasculature are characterized by a different expression of proteins and receptors if compared to the normal counterparts. Thereby, an approach to get better specificity to treat cancer or/and neoangiogenesis is the use of antibodies that can target specific antigens expressed in cancer or neo-endothelial cells or precursors that are not expressed or are expressed at a lower level on normal cells. These targets can be exploited using antibodies to kill antigen-bearing cells by inhibiting the biological activity of the antigen or by delivering immuno- or radio-conjugates that, when reach the antigen-bearing cells, specifically kill these target cells.

An example of such target is the cell membrane protein, named Endosialin.

Endosialin[2-4], is a highly restricted 165-kDa cell surface glycoprotein expressed by tumor pericytes and fibroblasts in a broad range of human cancers but not detected in the respective cell types in many normal tissues. The Endosialin cDNA encodes a type I membrane protein of 757 amino acids with a predicted molecular mass of 80.9 kDa. Bioinformatic evaluation classifies Endosialin as a C-type lectin-like protein, composed of a signal leader peptide, five globular extracellular domains (including a C-type lectin domain, one domain with similarity to the Sushi/ccp/scr pattern, and three EGF repeats), followed by a mucin-like region, a transmembrane segment, and a short cytoplasmic tail. Carbohydrate analysis shows that the Endosialin core protein carries abundantly sialylated, O-linked oligosaccharides and is sensitive to O-sialoglycoprotein endopeptidase, placing it in the group of sialomucin-like molecules. Endosialin was demonstrated to interact with proteins of the extracellular matrix (Fibronectin, Collagen I)[5] mediating cell adhesion and migration; another important Endosialin interactor is the tumor secreted protein, LGALS3BP[6], a protein involved in cell adhesion and migration, acting also as a pro-angiogenic factor[7].

The tumor vascular marker Endosialin/TEM1 is emerging as an attractive molecule for diagnostics and therapeutics because of its expression across the stroma of many human tumors, the low to absent expression in normal tissues, and accessibility from the vascular circulation. Smaller scFv constructs have also been reported for Endosialin targeting of drug-delivery vehicles[8] or diagnostics for fluorescence imaging techniques[9].

Endosialin is broadly expressed in human cancer[10]. Its frequency, extent, and intensity vary among cancer subtypes as well as among individual tumors within subtypes. Endosialin was detected in almost all sarcoma suggesting that the protein is a very frequent feature of sarcoma. In sarcoma, Endosialin was detected in several cellular compartments including malignant sarcoma cells, stromal cells, and vasculature. Sarcoma subtypes with the greatest frequency, extent, and intensity of Endosialin expression and potentially the most promising therapeutic potential were synovial sarcoma, fibrosarcoma, malignant fibrous histiocytoma (MFH), liposarcoma, and osteosarcoma. In addition to sarcoma, high Endosialin expression rate was observed in vasculature of carcinomas, with bladder cancer emerging as an outstanding carcinoma subtype for Endosialin expression. The restriction of Endosialin expression in carcinomas to vasculature and stromal has implications for potential Endosialin-directed therapeutics, which could be expected to have an antiangiogenic or vascular-disrupting mechanism of action. In contrast, in sarcomas, an Endosialin-targeted therapeutic could have both a direct anticancer effect on malignant sarcoma cells, and an indirect anticancer effect due to antiangiogenic and/or vascular disrupting effects. Furthermore, for tumors expressing Endosialin directly by cancer cells, a diagnostic assay that measures the intensity of Endosialin expression in malignant tissues would assist in selecting patients that could benefit from an anti-Endosialin therapy. Thus, Endosialin holds potential value both as a biomarker for certain human cancers, like sarcoma[10-11] and as a targeted therapeutic agent.

While several investigators have shown that Endosialin plays an important role in tumor growth and stromal expansion[12-14] with expression levels that have been correlated with tumor progression[15,16], the mechanisms by which Endosialin functions are substantially unknown. Maia. et al[17] reported that the cytoplasmic domain of Endosialin is a key regulator of tumor growth and that tumor growth of mice lacking this domain are significantly reduced, if compared to the response in CD248WT/WT mice. In addition, they found that Endosialin present in fibroblasts expressing the cytoplasmatic domain of Endosialin also had impaired PDGF-BB-induced migration.

Tomkowicz B et al[18] demonstrated that Endosialin mediates proliferation of primary human pericytes through a PDGF (platelet derived growth factor) receptor signaling pathway. Normal pericytes expressing high levels of Endosialin were able to proliferate, to respond to PDGF stimulation by phosphorylating both the PDGF receptor and the MAPK Erk1/2, and to induce the expression of the immediate early transcription factor c-Fos. In Endosialin knocked-down pericytes, PDGF-induced proliferation, Erk1/2 phosphorylation, and c-Fos expression were significantly impaired. These results indicated that Endosialin controls proliferation of human pericytes together with PDGF pathway and suggest that targeting this protein could represent a novel modality for mitigating tumor angiogenesis and suppressing cancer.

Altogether, experimental and clinical data indicate that Endosialin plays an essential role in tumor progression and angiogenesis, suggesting that agents targeting Endosialin could be useful as therapeutic and diagnostic tools for some cancers[19-23].

In spite of scientific progress and introduction into clinical practice of new chemotherapeutic agents and targeted therapies, cancer remains a disease difficult to cure, responsible for about 13% of deaths worldwide[24-26].

Consequently, there is an urgent need to develop new antitumor therapies, more effective and possibly less toxic.

The inventors have found that specific Endosialin inhibitors are able to inhibit tumor growth. In particular, the murine mMP-E-8.3, the chimeric cMP-E-8.3 and humanized hMP-E-8.3 monoclonal antibodies, have been used as anti-Endosialin inhibitors.

A first aspect of the invention is an antibody or functional fragment thereof which is directed against an epitope between amino acids 477-488 of human Endosialin according to SEQ ID NO: 1.

The invention also provides conjugates based on an antibody as herein described. In particular, an Antibody-Drug Conjugate (ADC) based on hMP-E-8.3 monoclonal antibody is an additional subject matter of the present invention.

The monoclonal antibody hMP-E-8.3 and the ADC thereof are suitable for use in medicine, particularly human medicine, more particularly for the diagnosis, prevention and/or treatment of neoplastic disorders and cancer.

ADC and Cancer Therapy

Despite extensive research, most anticancer drugs have important nonspecific toxicity. By targeting the cell cycle and thereby killing rapidly proliferating cells, they do not explicitly discriminate between healthy and tumor tissues and only gain a limited selectivity for malignant cells. Due to a lack of selectivity, drug concentrations that would eradicate the tumor can often not be used. In addition, tumors can develop resistance against anticancer drugs after prolonged treatment. Therefore, achieving improved tumor selectivity through targeting of cytotoxic drugs to the cancer cells is needed.

Antibody-drug conjugates (ADCs) are ideal candidates for easing this need. ADCs are monoclonal antibodies (mAbs) linked to cell-killing drugs. Thanks to their high binding specificity for tumor-specific antigens, mAbs can be used as vehicles to target lethal payloads to tumor cells [27-28] [1, 2]. Naked mAbs can also be used for the treatment of cancer, thanks to their ability to interrupt cell-survival signals and/or induce an immunological response against the target cancer cell. However, the therapeutic efficacy of naked mAbs is often limited. This can be circumvented by arming the immunoglobulin with cytotoxic drugs or radioactive isotopes, yielding highly specific ADCs.

This invention relates to an innovative ADC based on the humanized monoclonal antibody hMP-E-8.3, which specifically binds Endosialin, coupled to a payload consisting of a duocarmycin derivative by means of a cleavable linker. This payload belongs to DNA damaging agents, specifically to Minor Grove Binders.

The choice of Endosialin as the target for an ADC is justified by experimental and clinical data indicating that this glycosylated receptor is overexpressed in some tumors, such as sarcoma and neuroblastoma, but not in normal tissue.

A further aspect of the invention is a nucleic acid molecule encoding the antibody, optionally in operative linkage to an expression control sequence.

A further aspect of the invention is a host, in particular a recombinant cell which comprises the nucleic acid molecule. The cell may be used for the preparation of the antibody.

Still a further aspect of the invention is pharmaceutical composition comprising the antibody, the nucleic acid molecule or the host, optionally, together with a pharmaceutical acceptable carrier.

Still a further aspect of the invention is a method for the prevention or treatment of neoplastic diseases and cancer.

The term "antibody" particularly refers to molecules comprising at least one immunoglobulin heavy chain and at least one immunoglobulin light chain. Each heavy and light chain may comprise a variable and a constant domain. The antigen binding site may be formed from the variable domains of a heavy and light chain. A variable region (also referred to as variable domain) comprises complementarity determining regions (CDRs), e.g. a CDR1, a CDR2 and a CDR3 region and framework regions (FRs) flanking the CDRs. The term "complementarity determining region" is readily understood by the skilled person (see for example Harlow and Lane (eds.), Antibodies: A Laboratory Manual, CSHL press, Cold Spring Harbor, N.Y., 1988) and refers to the stretches of amino acids within the variable domain of an antibody that primarily make contact with the antigen and determined antibody specificity. This region is also known as the hypervariable region.

The invention also encompasses fragments of antibodies, e.g. portions of the above-mentioned antibodies which comprise at least one antigen binding site. Examples of antibody fragments include Fab fragments, Fab' fragments, F(ab')2 fragments, Fv fragments, diabodies, ScFv fragments, single chain antibody molecules, small modular immunopharmaceuticals (SMIPs), affibodies, avimers, nanobodies, domain antibodies and other fragments as long as they exhibit the desired capability of binding to human Endosialin. For a review of certain antibody fragments see Hudson et al., Nat. Met. 9: 129-134 (2003).

"Avimer" relates to a multimeric binding protein or peptide engineered using, for example, in vitro exon shuffling and phage display. Multiple binding domains are linked, resulting in greater affinity and specificity compared to single epitope immunoglobin domains.

"Nanobody" or single domain antibody relates to an antibody fragment consisting of a single monomeric variable antibody domain.

"Affibody" molecules are small high affinity proteins being engineered to bind specifically to a large number of target proteins.

"Diabodies" are antibody fragments with two antigen binding sites that may be bivalent or bispecific. See for example Hudson et al., (2003). Single-chain antibodies are antibody fragments comprising all or a portion of the heavy chain variable domain or all, or a portion of the light chain variable domain of an antibody. Antibody fragments can be made by various techniques including but not limited to proteolytic digestion of an intact antibody as well as production by recombinant hosts (e.g. *E. coli* or phage) as described herein.

In certain embodiments, an antibody provided herein is a multispecific antibody, e.g. a bispecific antibody. Multispecific antibodies are monoclonal antibodies that have binding specificities for at least two different sites.

In certain embodiments, one of the binding specificities is for human Endosialin as described above and the other is for LGALS3BP. The use of such a bi-specific antibody should be useful in order to inhibit to a greater extent tumor angiogenesis if compared to the effect of the single antibody treatments. The bi-specific antibody will act at the same time on endothelial cells angiogenesis (antibody against LGALS3BP) and/or tumor cells and pericytes (antibody against Endosialin).

Techniques for making multispecific antibodies include but are not limited to recombinant co-expression of two immunoglobulin heavy chain-light chain pairs having different specificities and "knob in hole" engineering. Multispecific antibodies may also be made by engineering electrostatic steering effects for making antibody Fc-heterodimeric molecules; crosslinking two or more antibodies or fragments; using leucine zippers to produce bispecific antibodies; using "diabody" technology for making bispecific antibodies and using single-chain Fv and preparing trispecific antibodies as described. Engineered antibodies with three or more functional antigen binding sites including "octopus antibodies" are also included herein.

In certain embodiments, amino acid sequence variants of the antibodies provided herein are contemplated as long as they exhibit the desired capability of binding to human Endosialin. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from and/or insertions into and/or substitutions of residues within the amino acid sequences of the antibody. Any combination of deletion, insertion and substitution can be made to arrive at the final construct, provided that the final construct possesses the desired characteristics, e.g. antigen binding.

The term "bind" or "binding" of an antibody means an at least temporary interaction or association with or to a target antigen, i.e. human Endosialin comprising fragments thereof containing an epitope, in particular an epitope between amino acids 477-488 of human Endosialin according to SEQ ID NO: 1.

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. $10^{-9}$ M to $10^{-13}$ M).

In one embodiment, Kd is measured by a radio-labeled antigen binding assay (Radioimmunoassay, RIA) performed with the Fab version of an antibody of interest and its antigen.

According to another embodiment, Kd is measured using surface plasmon resonance assays with immobilized antigen. According to a preferred embodiment of the present invention, the antibodies are human monoclonal antibodies directed against an epitope of human Endosialin as described herein.

The antibody may be any antibody of natural and/or synthetic origin, e.g. an antibody of mammalian origin. Preferably, the constant domain—if present—is a human constant domain. The variable domain is preferably a mammalian variable domain, e.g. a humanized or a human variable domain.

Antibodies according to the invention are preferably monoclonal antibodies. In particular, antibodies of the present invention are preferably recombinant murine antibodies, chimeric, humanized or fully human antibodies, multispecific antibodies, in particular bispecific antibodies, or fragments thereof.

Monoclonal antibodies may be produced by any suitable method such as that of Köhler and Milstein[27] or by recombinant DNA methods. Monoclonal antibodies may also be isolated from phage antibody libraries using techniques described in Clackson et al[28].

According to a preferred aspect of the invention, the antibodies of the invention are humanized antibodies, in particular fully human antibodies.

Humanized forms of the antibodies may be generated according to the methods known in the art such as chimerization or CDR grafting. Alternative methods for the production of humanized antibodies are well known in the art and are described in, e.g., EP-A1 0 239 400 and WO 90/07861. Human antibodies can also be derived by in vitro methods. Suitable examples include but are not limited to phage display, yeast display, and the like.

According the present invention "chimeric antibody" relates to antibodies comprising polypeptides from different species, such as, for example, mouse and human. The production of chimeric antibodies is described, for example, in WO 89/09622.

The antibody of the invention may be preferably of the IgG1, IgG2, IgG3, IgG4, IgM, IgA1, IgA2, IgAsec, IgD, and IgE antibody-type. It will be appreciated that antibodies that are generated need not initially possess such an isotype but, rather the antibody as generated can possess any isotype and that the antibody can be isotype-switched.

The antibodies or antibody fragments of the invention are optionally deimmunized for therapeutic purposes.

It will be apparent to those skilled in the art that the antibodies of the invention can be further coupled to other moieties for, e.g., drug targeting and imaging applications. Antibodies coupled to other moieties are also called "antibody conjugates". Coupling may be conducted chemically after expression of the antibody or antigen to site of attachment or the coupling product may be engineered into the antibody or antigen of the invention at the DNA level.

For diagnostic purposes, the antibody or antibody fragment of the invention may be labelled, i.e. coupled to a labelling group. Suitable labels include radioactive labels, fluorescent labels, suitable dye groups, enzyme labels, chromogenes, chemiluminescent groups, biotinyl groups, predetermined polypeptide epitopes recognized by a secondary reporter etc. Preferably, the labels are covalently bound to the antibody.

Those labelled antibodies or antibody fragments (also referred to as "antibody conjugates") may in particular be used in immunohistochemistry assays or for molecular imaging in vivo.

For therapeutic purposes, the antibody or antibody fragment of the invention may be conjugated with an effector group, in particular a therapeutic effector group such as a cytotoxic agent or a radioactive group agent.

The antibody of the present invention may optionally be coupled to a labeling group and/or to an effector group, preferably a therapeutic group. According to a preferred aspect of the invention, the antibody is linked to a paramagnetic, radioactive or fluorogenic ion that is detectable upon imaging. This type of antibody is particularly suitable for diagnostic use.

According to another aspect of the invention, the antibody is linked to an anticellular agent, preferably in the form of anti-mitotic or DNA damaging agents capable of killing or suppressing the growth or cell division of tumor cells. The anticellular agent may, for example, comprise a chemotherapeutic agent, radioisotope or cytotoxin. Examples of anticellular agents comprise an antimetabolite, an anthracycline, a vinca alkaloid, an antibiotic, an alkylating agent or a plant-, fungus- or bacteria-derived toxin. An exemplary DNA damaging agent that may be linked to the antibody of the invention is a Minor Grove Binder duocarmycin derivative. Cytotoxins suitable to be linked to the antibody of the invention may, for example, comprise an A chain toxin, a ribosome inactivating protein, α-sarcin, aspergillin, restrictocin, a ribonuclease, diphtheria toxin or *Pseudomonas* exotoxin. Further, the cytotoxin may comprise deglycosylated ricin A chain.

Labelling groups or effector groups may be attached by linkers (spacer arms) of various lengths to reduce potential steric hindrance. Effector groups may be also attached directly to the antibody.

The inventors of the present application found that antibodies directed against an epitope between amino acids 477-488 of human Endosialin according to SEQ ID NO: 1 or functional fragments or functional derivatives thereof are particularly useful for therapeutic and diagnostic applications. The epitope recognized by the antibody of the invention is located in the extracellular domain of human Endosialin.

It was surprisingly found that the antibodies of the present invention show advantageous properties with respect to their biological activity. It was found that binding of antibodies to Endosialin inhibits PDGF-signalling in pericytes. Further, antibodies of the invention have the ability to internalize in Endosialin-positive cell lines. They have the ability to block in vitro tube formation induced by LGALS3BP. Moreover, they are able to inhibit tumor growth in sarcoma xenografts alone or in combination with an antibody against LGALS3BP. It was found that these properties are especially distinct with the antibodies described in the following that are characterized by certain complementarity determining regions.

In certain embodiments of the present invention, the antibody may comprise specific heavy chain complementarity determining regions CDRH1, CDRH2 and/or CDRH3 as described herein below.

In one embodiment, the human antibody comprises a heavy chain complementarity determining region 1 (CDRH1) having the amino acid sequence as shown in SEQ ID NO: 2, or an amino acid sequence differing in 1 or 2 amino acids therefrom.

According to a preferred embodiment, CDRH1 has a sequence as shown in SEQ ID NO: 26 or an amino acid sequence differing in 1 or 2 amino acids therefrom.

In a further embodiment, the antibody comprises a heavy chain complementarity determining region 2 (CDRH2) having the amino acid sequence as shown in SEQ ID NO: 3, or an amino acid sequence differing in 1 or 2 amino acids therefrom.

In yet a further embodiment, the antibody comprises a heavy chain complementarity determining region 3 (CDRH3) having the amino acid sequence as shown in SEQ ID NO: 4, or an amino acid sequence differing in 1 or 2 amino acids therefrom.

The antibody according to the invention may also comprise specific light chain complementarity determining regions CDRL1, CDRL2 and/or CDRL3.

Accordingly, in one embodiment, the antibody comprises a light chain complementarity determining region 1 (CDRL1) having the amino acid sequence as shown in SEQ ID NO: 5, or an amino acid sequence differing in 1 or 2 amino acids therefrom.

In a further embodiment, the antibody comprises a light chain complementarity determining region 2 (CDRL2) having the amino acid sequence as shown in SEQ ID NO: 6, or an amino acid sequence differing in 1 or 2 amino acids therefrom.

In yet a further embodiment, the antibody comprises a light chain complementarity determining region 3 (CDRL3) having the amino acid sequence as shown in SEQ ID NO: 7, or an amino acid sequence differing in 1 or 2 amino acids therefrom.

The antibody of the present invention may preferably comprise a specific combination of CDRs (i.e. of CDRH1, CDRH2 and CDRH3) within one heavy chain.

Accordingly, in one preferred embodiment, the antibody comprises a heavy chain comprising complementarity determining regions CDRH1, CDRH2 and CDRH3, wherein CDRH1 has the amino acid sequence as shown in SEQ ID NOs: 2, or an amino acid sequence differing in 1 or 2 amino acids therefrom, CDRH2 has the amino acid sequence as shown in SEQ ID NOs: 3, or an amino acid sequence differing in 1 or 2 amino acids therefrom, and CDRH3 has the amino acid sequence as shown in SEQ ID NOs: 4, or an amino acid sequence differing in 1 or 2 amino acids therefrom.

According to the present invention, it is further preferred that the antibody comprises a specific combination of CDRs within one light chain (i.e. of CDRL1, CDRL2 and CDRL3).

Thus, in one preferred embodiment, the antibody comprises a light chain comprising complementarity determining regions CDRL1, CDRL2 and CDRL3, wherein CDRL1 has the amino acid sequence as shown in SEQ ID NOs: 5, or an amino acid sequence differing in 1 or 2 amino acids therefrom, CDRL2 has the amino acid sequence as shown in SEQ ID NO: 6, or an amino acid sequence differing in 1 or 2 amino acids therefrom, and CDRL3 has the amino acid sequence as shown in SEQ ID NO: 7, or an amino acid sequence differing in 1 or 2 amino acids therefrom.

As described above, the complementarity determining regions (CDRs) of an antibody may be flanked by framework regions. A heavy or light chain of an antibody containing three CDRs contains e.g. four framework regions.

Additionally, the present invention also encompasses those antibodies that recognize the same epitope on human Endosialin as a specific antibody characterized by the above heavy and/or light chain CDRs. Functional fragments and functional derivatives of those antibodies are also within the scope of the invention.

To determine the epitope on Endosialin recognized by the antibody, chemically prepared arrays of protein sequence derived short peptides derived from the amino acid sequence of the extracellular domain of human Endosialin can be used to locate and identify antibody epitopes (Reinicke W., Methods Mol. Biol. 2004, 248: 443-63). A further method to map the epitopes in the Endosialin extracellular domain bound by the antibodies of the invention comprises Snaps/SELDI (Wang et al., Int. J. Cancer, 2001, Jun. 15; 92 (6): 871-6) or a routine cross-blocking assay such as described in Antibodies, A Laboratory Manual, Cold Spring Harbor Laboratory, Ed Harlow and David Lane (1988) can be performed.

According to a particularly preferred embodiment of the present invention, the antibody comprises:
(i) a heavy chain comprising:
  a heavy chain complementarity determining region 1 (CDRH1) having the amino acid sequence as shown in SEQ ID No: 2 or an amino acid sequence differing in 1 or 2 amino acids therefrom,
  a heavy chain complementarity determining region 2 (CDRH2) having the amino acid sequence as shown in SEQ ID No: 3 or an amino acid sequence differing in 1 or 2 amino acids therefrom, and
  a heavy chain complementarity determining region 3 (CDRH3) having the amino acid sequence as shown in SEQ ID No: 4 or an amino acid sequence differing in 1 or 2 amino acids therefrom, and
(ii) a light chain comprising:
  a light chain complementarity determining region 1 (CDRL1) having the amino acid sequence as shown in SEQ ID No: 5 or an amino acid sequence differing in 1 or 2 amino acids therefrom,
  a light chain complementarity determining region 2 (CDRL2) having the amino acid sequence as shown in SEQ ID No: 6 or an amino acid sequence differing in 1 or 2 amino acids therefrom, and
  a light chain complementarity determining region 3 (CDRL3) having the amino acid sequence as shown in SEQ ID No: 7 or an amino acid sequence differing in 1 or 2 amino acids therefrom,
or a monoclonal antibody recognizing the same epitope on human Endosialin.

Preferably, the CDR sequences are selected from those shown in SEQ ID NOs: 2-7 without any variation.

In particular, the antibody may comprise the heavy chain complementary determining regions CDRH1-3 as shown in SEQ ID NOs: 2, 3 and 4, and the light chain complementarity determining regions CDRL1-3 as shown in SEQ ID NOs: 5, 6 and 7.

In a preferred embodiment of the invention, the antibody comprises a heavy chain variable region (VH) as shown in SEQ ID NO8, or a sequence differing in one or two amino acids therefrom. Further, the antibody of the invention preferably comprises a light chain variable region (VL) as shown in SEQ ID NO: 9, or a sequence differing in one or two amino acids therefrom. Further, the present invention also encompasses those antibodies that comprise an amino acid sequence having a sequence identity of at least 90% to the heavy chain variable region as shown in SEQ ID NO: 8 and/or to the light chain variable region as shown in SEQ ID NO: 9, preferably at least 95% sequence identity over the whole length. Particularly preferred are antibodies comprising a heavy chain variable region as shown in SEQ ID NO: 8 and a light chain variable region as shown in SEQ ID NO: 9.

According to a particularly preferred embodiment of the invention, the antibody of the invention comprises a heavy chain comprising an amino acid sequence as shown in SEQ ID NO: 10 or 11, or an amino acid sequence having a sequence identity of at least 90% thereto over the whole length, and a light chain comprising an amino acid sequence as shown in SEQ ID NO: 12 or 13, or an amino acid sequence having a sequence identity of at least 90% thereto over the whole length. The sequence identity of the heavy chain and the light chain amino acid sequence is preferably at least 95% to the sequences shown in SEQ ID NOs: 10, 11, 12 and 13, respectively. Most preferred is an antibody comprising the heavy chain amino acid sequence as shown in SEQ ID NO: 10 and the light chain amino acid sequence as shown in SEQ ID NO: 12, as well as an antibody comprising the heavy chain amino acid sequence as shown in SEQ ID NO: 11 and the light chain amino acid sequence as shown in SEQ ID NO: 13.

In particular, preferred are humanized antibodies, especially monoclonal humanized antibodies.

A particular preferred embodiment of the present invention relates to an antibody comprising
a heavy chain variable region comprising an amino acid sequence as shown in SEQ ID NO: 18, SEQ NO: 19, SEQ ID NO: 20 or SEQ ID NO: 21 or an amino acid sequence having a sequence identity of at least thereto, and/or
a light chain variable region comprising a human acid sequence as shown in SEQ ID NO: 22, SEQ ID NO: 23, SEQ ID NO: 24 or SEQ ID NO: 25 or an amino acid sequence having a sequence identity of at least 90% thereto.

According to a further preferred embodiment, the present invention relates to a humanized antibody having a heavy chain variable region comprising the amino acid according to SEQ ID NO: 18 or an amino acid sequence having a sequence identity of at least 90% thereto, and a light variable chain region comprising an amino acid sequence as shown in SEQ ID NO: 22 or an amino acid sequence having a sequence identity of at least 90% thereto.

In another preferred embodiment, the present invention relates to a humanized antibody having a heavy chain variable region comprising the amino acid according to SEQ ID NO: 19 or an amino acid sequence having a sequence identity of at least 90% thereto, and a light variable chain region comprising an amino acid sequence as shown in SEQ ID NO: 23 or an amino acid sequence having a sequence identity of at least 90% thereto.

Also a preferred embodiment of the invention is a humanized antibody having a heavy chain variable region comprising the amino acid according to SEQ ID NO: 20 or an amino acid sequence having a sequence identity of at least 90% thereto, and a light variable chain region comprising an amino acid sequence as shown in SEQ ID NO: 24 or an amino acid sequence having a sequence identity of at least 90% thereto.

According to a further preferred embodiment, the present invention relates to a humanized antibody having a heavy chain variable region comprising the amino acid according to SEQ ID NO: 21 or an amino acid sequence having a sequence identity of at least 90% thereto, and a light variable chain region comprising an amino acid sequence as shown in SEQ ID NO: 25 or an amino acid sequence having a sequence identity of at least 90% thereto.

According to a preferred embodiment of the present invention, the antibody recognizes human Endosialin expressed on the cell surfaces of tumor vascular cells to a greater degree than on the surfaces of normal endothelial cells. Preferably, the antibody is further defined as a bispecific antibody that recognizes the human tumor-associated antigen LGALS3BP (aka Mac-2 BP or 90K).

According to another aspect, the present invention relates to a nucleic acid molecule encoding the antibody of the invention or fragment thereof or a nucleic acid capable of hybridizing thereto under stringent conditions. The nucleic acid molecule of the invention encoding the above-described antibody, antibody fragment or derivative thereof may be, e.g. DNA, cDNA, RNA or synthetically produced DNA or RNA or recombinantly produced chimeric nucleic acid molecule comprising any of those nucleic acid molecules either alone or in combination. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions or additions. In a particular preferred embodiment of the present invention, the nucleic acid molecule is a cDNA molecule.

According to the present invention, an isolated nucleic acid molecule of the present invention is particularly selected from the group consisting of:
 (a) a nucleic acid sequence encoding an antibody, antibody fragment or a derivative thereof as disclosed herein, preferably a nucleic acid sequence as shown in any one of SEQ ID NOs: 14-15 and SEQ ID NOs. 16-17 or SEQ ID NOs: 18-25,
 (b) a nucleic acid sequence complementary to any of the sequences in (a); and
 (c) a nucleic acid sequence capable of hybridizing to (a) or (b) under stringent conditions.

The term "hybridizing under stringent conditions" means that two nucleic acid fragments hybridize with one another under standardized hybridization conditions as described for example in Sambrook et al., "*Expression of cloned genes in E. coli*" in Molecular Cloning: A laboratory manual (1989), Cold Spring Harbor Laboratory Press, New York, USA. Such conditions are for example hybridization in 6.0×SSC at about 45° C. followed by a washing step with 2.0×SSC at 50° C., preferably 2.0×SSC at 65° C., or 0.2×SSC at 50° C., preferably 0.2×SSC at 65° C.

Another aspect of the invention relates to a vector comprising a nucleic acid molecule of the invention. Said vector may be, for example, a phage, plasmid, viral or retroviral vector. Retroviral vectors may be replication competent or replication defective. Preferably, the vector of the invention is an expression vector wherein the nucleic acid molecule is operatively linked to one or more control sequences allowing the transcription and optionally expression in prokaryotic and/or eukaryotic host cells.

The invention further relates to a host comprising the vector of the invention. Said host may be a prokaryotic or eukaryotic cell or a non-human transgenic animal. The polynucleotide or vector of the invention which is present in the host may either be integrated into the genome of the host or it may be maintained extra chromosomally.

The host can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*.

The invention additionally relates to a method for the preparation of an antibody, comprising culturing the host of the invention under conditions that allow synthesis of said antibody and recovering said antibody from said culture.

A further aspect of the present invention relates to a pharmaceutical composition comprising the antibody of the invention or a fragment thereof, the nucleic acid molecule, the vector, the host of the invention or an antibody obtained by a method of the invention. The term "composition" as employed herein comprises at least one compound of the invention. Preferably, such a composition is a therapeutic/pharmaceutical or a diagnostic composition.

The diagnostic composition of the invention may be used for assessing the onset or the disease status of a cancer.

The composition preferably comprises a pharmaceutically acceptable carrier, diluent and/or excipient.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers, excipients and/or diluents can be formulated by well-known conventional methods.

Administration of the suitable compositions may be effected by different ways, e.g., by intravenous, intraperitoneal, subcutaneous, intramuscular, topical, intradermal, intranasal or intra-bronchial administration. Preferred is an intravenous, intramuscular and/or subcutaneous administration.

These pharmaceutical compositions can be administered to the subject at a suitable dose. The dosage regimen can be determined by the attending physician and clinical factors.

The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition.

According to an especially preferred embodiment the composition comprises a further active agent, such as a further antibody or antibody fragment.

Preferably the composition of the invention is used in combination with at least one further antineoplastic agent. Said combination is effective, for example, in inhibiting abnormal cell growth. Many antineoplastic agents are presently known in the art. In general the term includes all agents that are capable of prevention, alleviation and/or treatment of hyperproliferative disorders, especially cancer.

Preferably the antineoplastic agent is selected from the group consisting of antibodies, small molecules, antimetabolites, alkylating agents, topo-isomerase inhibitors, microtubule-targeting agents, kinase inhibitors, protein synthesis inhibitors, immuno-therapeutics, hormones or analogs thereof.

Specific examples of antineoplastic agents which can be used in combination with the antibodies provided herein include, for example, chemotherapeutic agents such as Paclitaxel, Anthracyclines, Fluoropirimidine, vinca alkaloids, platinum salts, in particular capecitabine, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, melphalan, cyclophosphamide, 6-mercaptopurine, 6-thioguanine, cytarabine (CA), 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES).

According to an especially preferred embodiment, the further active agent is an inhibitor or LGALS3BP, e.g. an anti-LGALS3BP antibody or functional fragment thereof. This combination is particularly effective for inhibiting tumor angiogenesis.

The compositions of the invention may be administered in combination with a further therapeutic composition comprising an active agent as described above and/or irradiation and/or radiotherapy.

According to a preferred embodiment, the compositions of the invention are for the use in treating and/or preventing neoplastic diseases or cancer. The compositions may also be used for the manufacture of a medicament for treating and/or preventing neoplastic diseases or cancer.

The neoplastic diseases is preferably selected from disorders associated with, accompanied by Endosialin expression in tumor stroma and vasculature, or in cancer cells itself, in particular sarcoma (synovial sarcoma, fibrosarcoma, MFH, liposarcoma, osteosarcoma), neuroblastoma, high-grade glioma, brain tumors, carcinoma (bladder cancer, breast cancer, colorectal cancer, renal cancer, gastric cancer, endometrial cancer, lung cancer, ovarian cancer) and for all tumors expressing Endosialin in tumor vasculature and stroma and/or in tumor cells.

The invention further relates to a method of treating a disease wherein the antibody of the invention is administered to a mammal and wherein said disease is correlated directly or indirectly with an expression of Endosialin in tumor stroma or vasculature and/or tumor cell.

BRIEF DESCRIPTION OF THE DRAWINGS

FIG. 1 shows: (A) protein sequence of the target protein. (B) sequence of the different peptides use for immunization of the mice.

FIG. 8 shows hMP-E-8.3 humanized sequences.

EXAMPLES

Example 1

Production of the Monoclonal Antibody mMP-E-8.3

Four-weeks old Balb/c mice were immunized by intraperitoneal injection as emulsions in Complete Freund's Adjuvant (CFA) or Incomplete Freund's Adjuvant (IFA). Seven days later, mice were given an additional intraperitoneal injection of the immunogen. After additional seven days, mice were boosted intravenously with the immunogen, and spleens were removed for cell fusion 3 days later. Somatic cell hybrids were prepared by fusion of immune splenocytes with the murine non-secreting myeloma cell line NS-1. Hybridoma supernatants were selected with Elisa assay towards the respective peptide. All positive hybridoma cell colonies were cloned twice by limiting dilution and further characterized.

In FIG. 1A shows the sequence of the target protein; in FIG. 1B, a list of the peptides used for immunization (sequence of peptide of mMP-E-8.3 highlighted). All positive hybridoma supernatants were checked in ELISA for antigen affinity, and mMP-E-8.3 was selected as the antibody that recognised the antigen with higher affinity.

Figure 2:
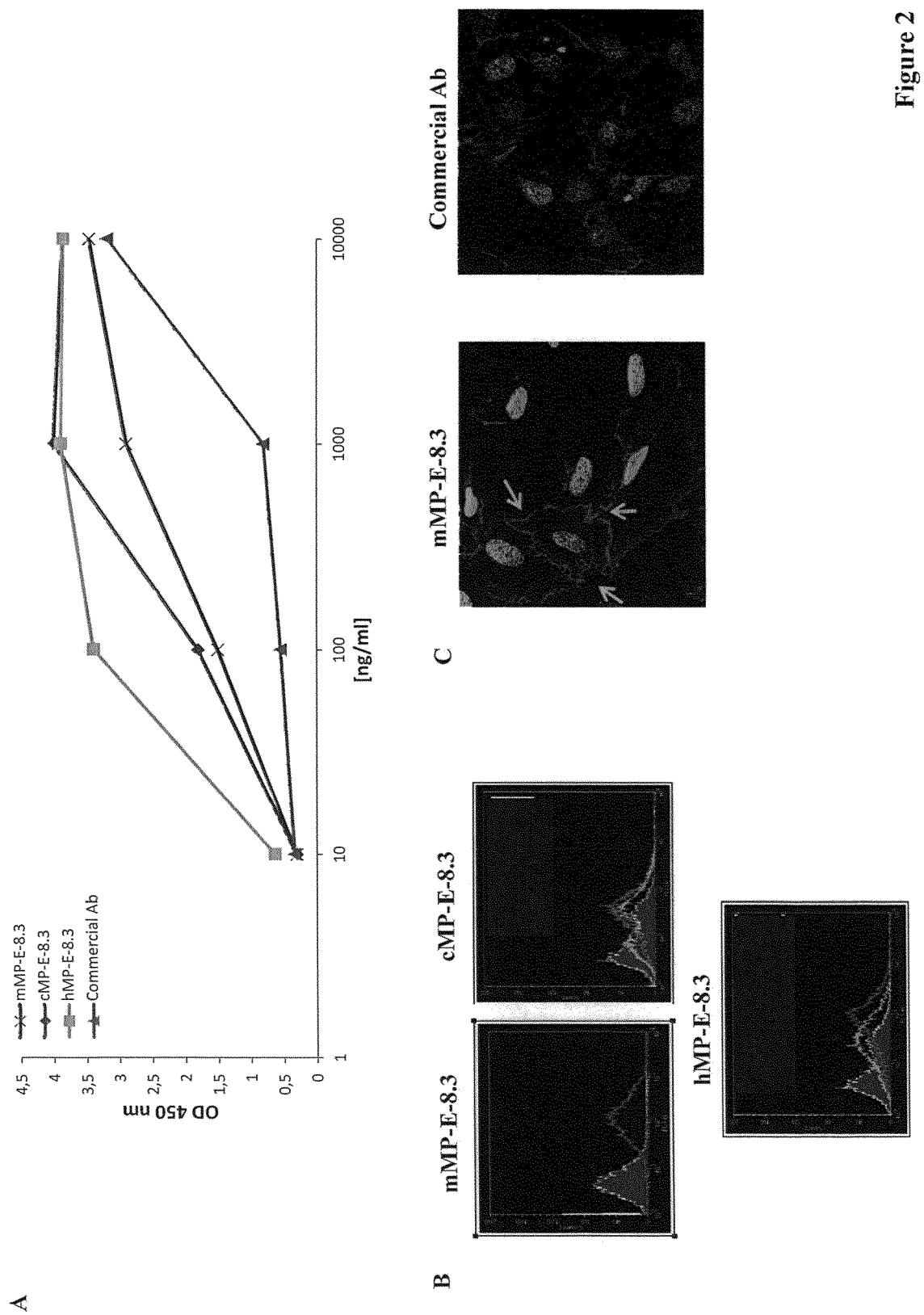
FIG. 2 shows that mMP-E-8.3, cMP-E-8.3 and the selected humanized antibody hMP-E-8.3 recognize human recombinant Endosialin by ELISA (2A) and flow cytometer (2B); and for mMP-E-8-3, also by laser scanning confocal microscopy (2C).

Example 2 mMP-E-8.3, cMP-E-8.3 and hMP-E-8.3 are Able to Recognize Endosialin by ELISA; mMP-E-8.3 by Flow Cytometer and Confocal Microscopy Materials and Methods: (FIG. 2). (A) Ninety-six well plates (NUNC Maxisorp modules) were pre-coated with human recombinant Endosialin (1 µg/ml) overnight at 4° C. After blocking with 1% BSA in PBS+0.1% Tween-20 for 1 hour at 4° C., mMP-E-8.3, cMP-E-8.3, hMP-E-8.3 and a commercial antibody against Endosialin at the indicated concentration were added and incubated for 2 hours at room temperature. After several washes with PBS+0.1% Tween-20, a goat anti-mouse or anti-human IgG-HRP solution was added to each well and incubated for 1 hour at 37° C. After washes, stabilized chromogen was added to each well for at least 10 minutes in the dark, then the reaction was stopped with the addition of 1 N $H_2SO4$ and the absorbance was read at 450 nm with an ELISA reader. (B) Sjsa-1 human osteosarcoma cell line were stained with 1 µg/ml of mMP-E-8.3 antibody, or cMP-E-8.3 and hMP-E-8.3 at 100 ng/ml (blue line) and 1 ug/ml (green line) or with 1 µg/ml of a commercial antibody against Endosialin on ice for 30 minutes after incubation with a Goat anti-mouse/anti-human Alexa- 488 conjugated antibodies for 1 hour on ice, cells were analyzed by flow cytometer (FACS). (C) Sjsa-1 human osteosarcoma cells were grown on glass coverslips for 24 hours. Cells were then fixed in 4% paraformaldehyde for 15 minutes at room temperature, permeabilized with 0.25% Triton X-100 for 5 minutes, and blocked with 0.1% BSA for 1 hour at room temperature. Coverslips were incubated for 2 hours at room temperature with mMP-E-8.3 or a commercial antibody, followed by goat anti-mouse secondary antibody Alexa Fluor 488 conjugated. DRAQ5 was used to visualize nuclei. Images were acquired with a Zeiss LSM 510 meta-confocal microscope using 488- and 633-nm lasers. The yellow arrows indicate that mMP-E-8.3 recognize Endosialin present on the cell plasma membrane.

Results: mMP-E-8.3, cMP-E-8.3 and the selected humanized variant hMP-E-8.3 recognize Endosialin by ELISA and flow-cytometer; murine, antibody was able to recognize human Endosialin expressed by Sjsa-1 cells by laser scanning confocal microscopy (FIG. 2C)

Example 3 mMP-E-8.3 Internalization in Sisa-1 Human Osteosarcoma Cell Line

Figure 3:
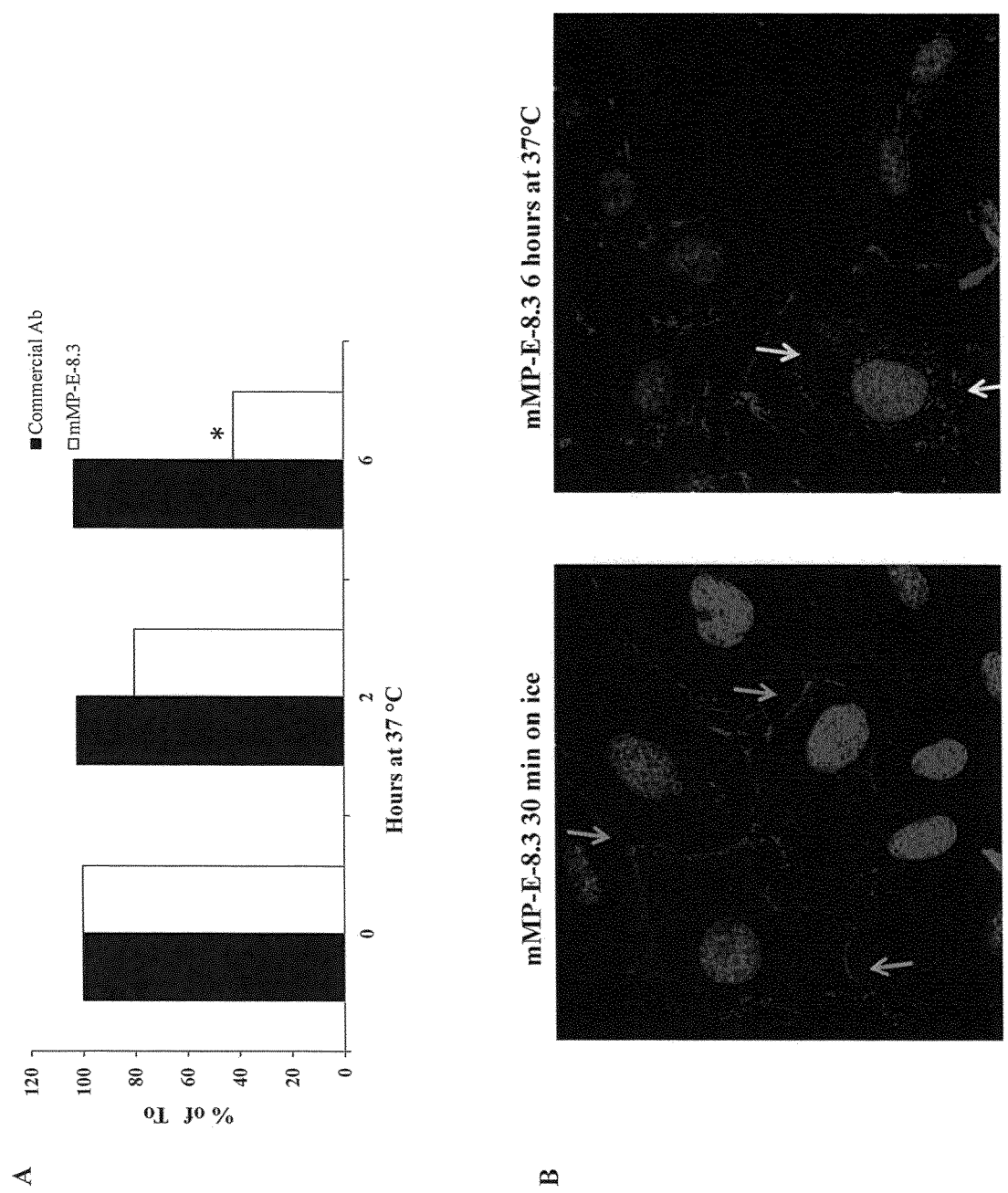
FIG. 3 shows that mMP-E-8.3 internalizes in Sjsa-1 Endosialin positive cells by flow cytometer (3A) and by laser scanning confocal microscopy (3B).

Materials and Methods: (FIG. 3). Sjsa-1 cells were plated in 12 well-plates and grown in 10% FBS RPMI-1640 for 24 hours. Cells were then incubated with 10 µg/ml of mMP-E-8.3, for 30 minutes on ice and returned at 37° C. for 6 hours. (A) After 6 hours, cells were stained with a goat anti-mouse Alexa 488-conjugated secondary antibody and analysed by FACS. (B) After 6 hours, cells were fixed in 4% paraformaldehyde, permeabilized with 0.2% Triton-X100 in PBS and then stained with a fluorescein-labeled goat anti-mouse/anti-human antibody (green staining). Cell nuclei were counterstained in blue. The yellow and the white arrows indicate antibody localization at the cell membrane and the cytoplasm, respectively.

Results: (A) Sjsa-1 cells show goat anti mouse membrane positivity after 30 minutes of mMP-E-8.3 incubation on ice indicating that the antibody is completely localized on the plasma membrane. After 6 hours at 37° C., the goat anti-mouse signals is reduced by 60% indicating that mMP-E-8.3 has been internalized by cells. (B) Sjsa-1 cells show goat anti-mouse membrane positivity (yellow arrows) after 30 minutes of mMP-E-8.3 incubation on ice indicating that the antibody is completely localized on the plasma membrane. After 6 hours at 37° C., the goat anti mouse signals present inside the cells, in particular in the peri-nuclear region (white arrows).

Example 4 mMP-E-8.3 Blocked PDGF Signaling in Human Pericytes

Figure 4:
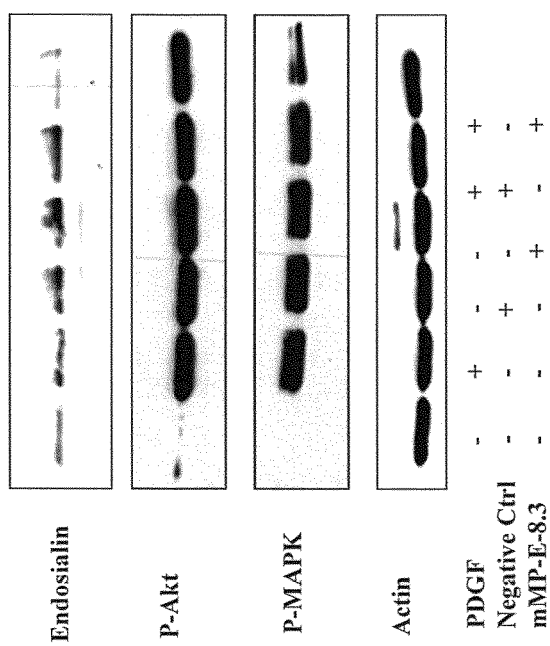
FIG. 4 shows that mMP-E-8.3 inhibits the phosphorylation of MAPK Erk1/2 in PDGF stimulated human pericytes.

Materials and methods: (FIG. 4). T/G HA-VSMC, a human vascular smooth muscular cell line were seeded for 24 hours in 12 well-plates, then were serum starved for 2 hours in pericyte's culture medium lacking serum and growth factors. Cells were then incubated with 10 µg/ml of mMP-E-8.3 antibody or a negative control antibody for 2 hours and then stimulated for 15 minutes with PDGF-BB (100 ng/mL). Cells were lysed directly with RIPA buffer and 30 µg of total lysates were subjected to western blot analysis to detect Endosialin, the phosphorylated form of Akt and MAPK. Actin was using as a loading control.

Results: Cells pre-treated with mMP-E-8.3 exhibit an inhibition of MAPK phosphorylation induced by PDGF treatment (FIG. 4)

Example 5

Production of Chimerized and Humanized Versions of the mMP-E-8.3 Antibody

Methods for humanizing non-human antibodies are well known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers[29-32], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some framework region (FR) residues are substituted by residues from analogous sites in rodent antibodies.

To produce the chimerized version of mMP-E-8.3 antibody (called cMP-E-8.3), hybridoma cells producing the mMP-E-8.3 were expanded, total RNA extracted and RT-PCR performed to clone and sequence the variable regions of the antibody using conventional procedures (e.g., by using oligonucleotide probes that are capable of binding specifically to genes encoding the heavy and light chains of murine antibodies).

For antibody chimerization, the murine constant regions were replaced with the human constant regions. It is a G1m17 IgG1 allotype with a human km3 kappa LC.

For antibody humanization, Complementarity Determining Regions (CDRs) from the murine were grafted in to a human antibody framework. Four humanized version of the heavy chain (HC) and light chain (LC) were designed and combined, obtaining the following antibody variants:

8.3-LIBR-H1L1 (No. E02999)
8.3-LIBR-H1L2 (No. E03000)
8.3-LIBR-H1L3 (No. E03001)
8.3-LIBR-H1L4 (No. E03002)
8.3-LIBR-H2L1 (No. E03003)
8.3-LIBR-H2L2 (No. E03004)
8.3-LIBR-H2L3 (No. E03005)
8.3-LIBR-H2L4 (No. E03006)
8.3-LIBR-H3L1 (No. E03007)
8.3-LIBR-H3L2 (No. E03008)
8.3-LIBR-H3L3 (No. E03009)
8.3-LIBR-H3L4 (No. E03010)
8.3-LIBR-H4L1 (No. E03011)
8.3-LIBR-H4L2 (No. E03012)
8.3-LIBR-H4L3 (No. E03013)
8.3-LIBR-H4L4 (No. E03014)
8.3-LIBR-H1L2 (No. E03000) was chosen as the best candidate based on affinity, antibody titer and stability.

Example 6

Prognostic Value of Endosialin in Human Colorectal Cancer

Materials and methods: Endosialin expression was analyzed in human primary colorectal cancer, diagnosed without lymph-node or distant metastases, from 175 patients by immunohistochemistry on Tissue Micro Arrays (TMAs). Results were correlated with patients outcome. One hundred forty-two (81.1%) patients had colon cancer and 33 (18.9%) had rectal cancer. One hundred twelve patients were males (64.0%) and 63 patients were females (36.0%). The median age of the patients at the time of diagnosis was 70 years (range 36-90). The median follow-up time was 54.0 months (range 3-238). Five-micron TMA sections were prepared for immunohistochemical staining. Staining was made by using anti-endosialin (TEM1) rabbit polyclonal antibody (Novus Biological) and anti-LGALS3BP mouse monoclonal antibody 1A422. Antigen retrieval was performed by microwave treatments at 750 W (10 min) in citrate buffer (pH 6.0). The anti-rabbit or anti-mouse EnVision kit (Dako) was used for signal amplification. To exclude unspecific staining, non-immune serum was included. The relationship between Endosialin expression and clinicopathologic characteristics of the patients was assessed by $\chi^2$ test. Survival analysis was done by the Kaplan-Meier method and the groups were compared with the log-rank test. Statistical procedures were done using SPSS version 15.0 (SPSS Inc.). P<0.05 was considered as statistically significant.

Figure 5:
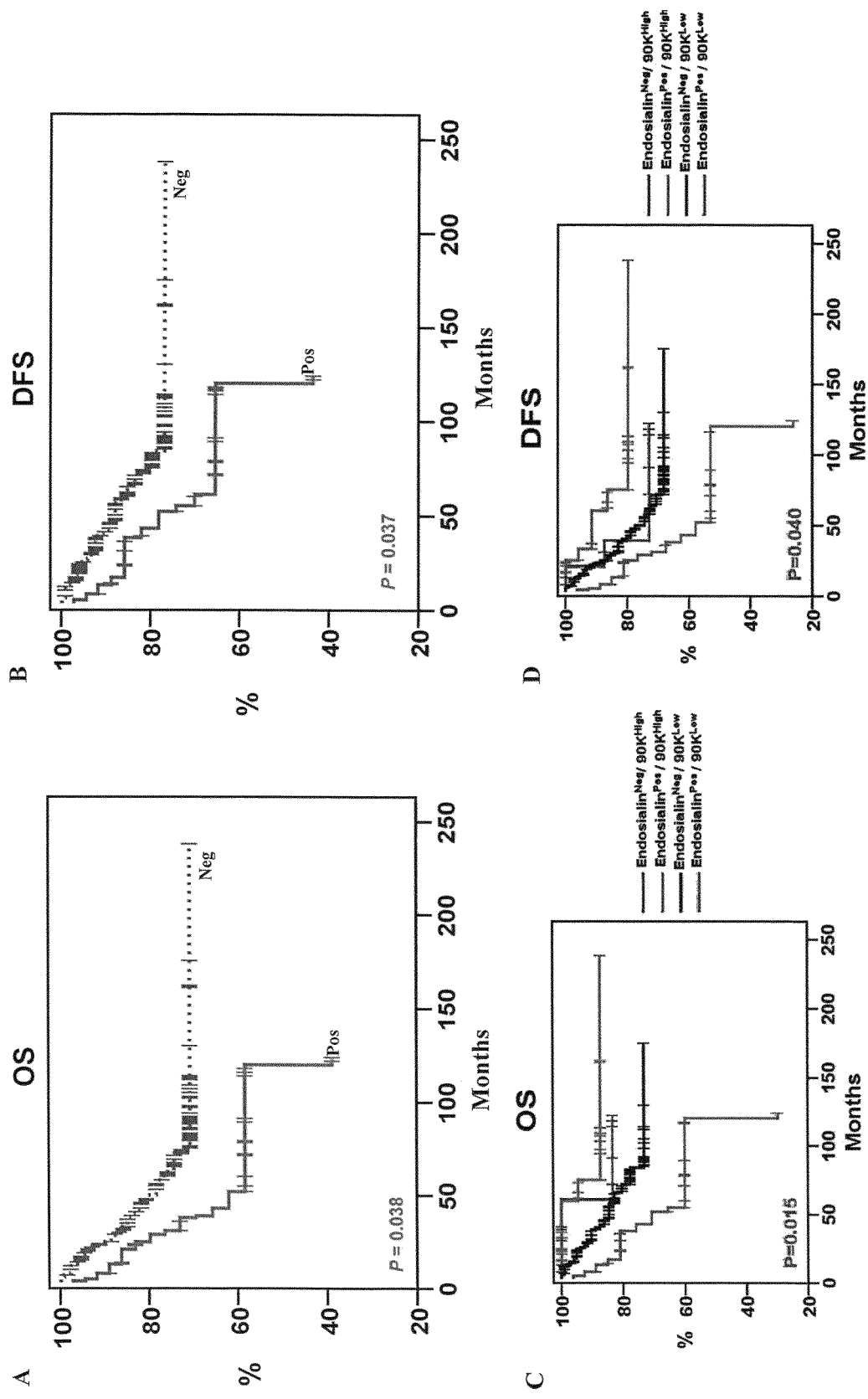
FIG. 5 shows that Endosialin status (positive versus negative) identifies patients with shorter DFS (A) and OS rate (B). The prognostic role of Endosialin status on survival (DFS and OS) was also examined in the context of LGALS3BP status (high versus low) (C,D).

Results: Thirty-seven out of 175 (21.1%) cases expressed Endosialin in the cytoplasm of tumor cells which also coexisted with a specific positive staining of stromal cells in 11 out of 37 (29.7%) positive cases. The proportion of Endosialin positive tumor cells was in the range of 4 to 100%, with a mean±SE of 45.4±5.3. All these cases were considered Endosialin positive. Statistical analysis revealed no relationship between Endosialin protein expression and any of the clinicopathological parameters evaluated. A disease relapse was observed in 37.8% (14/37) of patients with Endosialin positive, and in 21.0% (29/138) of those with Endosialin negative tumors. Death occurred in 29.7% and 13.9% of patients with positive and negative Endosialin tumors, respectively. At Kaplan-Meier analyses, expression of Endosialin was significantly associated with a lower OS (P=0.037) (FIG. 5A) and DFS (P=0.038) (FIG. 5B).

As LGALS3BP is an Endosialin binding partner[6] and the inventors developed a humanized monoclonal antibody against LGALS3BP (Use of anti-90k monoclonal antibodies for the prevention and treatment of tumors and metastases thereof WO 2010097825 A1), the prognostic role of Endosialin expression on survival (DFS and OS) was also examined in the context of LGALS3BP status. LGALS3BP was found to be a negative prognostic factor in the majority of human cancers, except in colon carcinoma where LGALS3BP lower expression in CRC tissues was found as a marker of poor prognosis.

Endosialin positivity identified patients with lower OS and DFS rate (FIGS. 5C and D) in LGALS3BP low expression cases (P=0.015 and P=0.040, respectively). Conversely, LGALS3BP high expression identified patients at significantly lower probability of relapse and death in Endosialin negative cases.

Example 7

Effect of cMP-E-8.3 on Tube Formation on Matrigel

Figure 6:
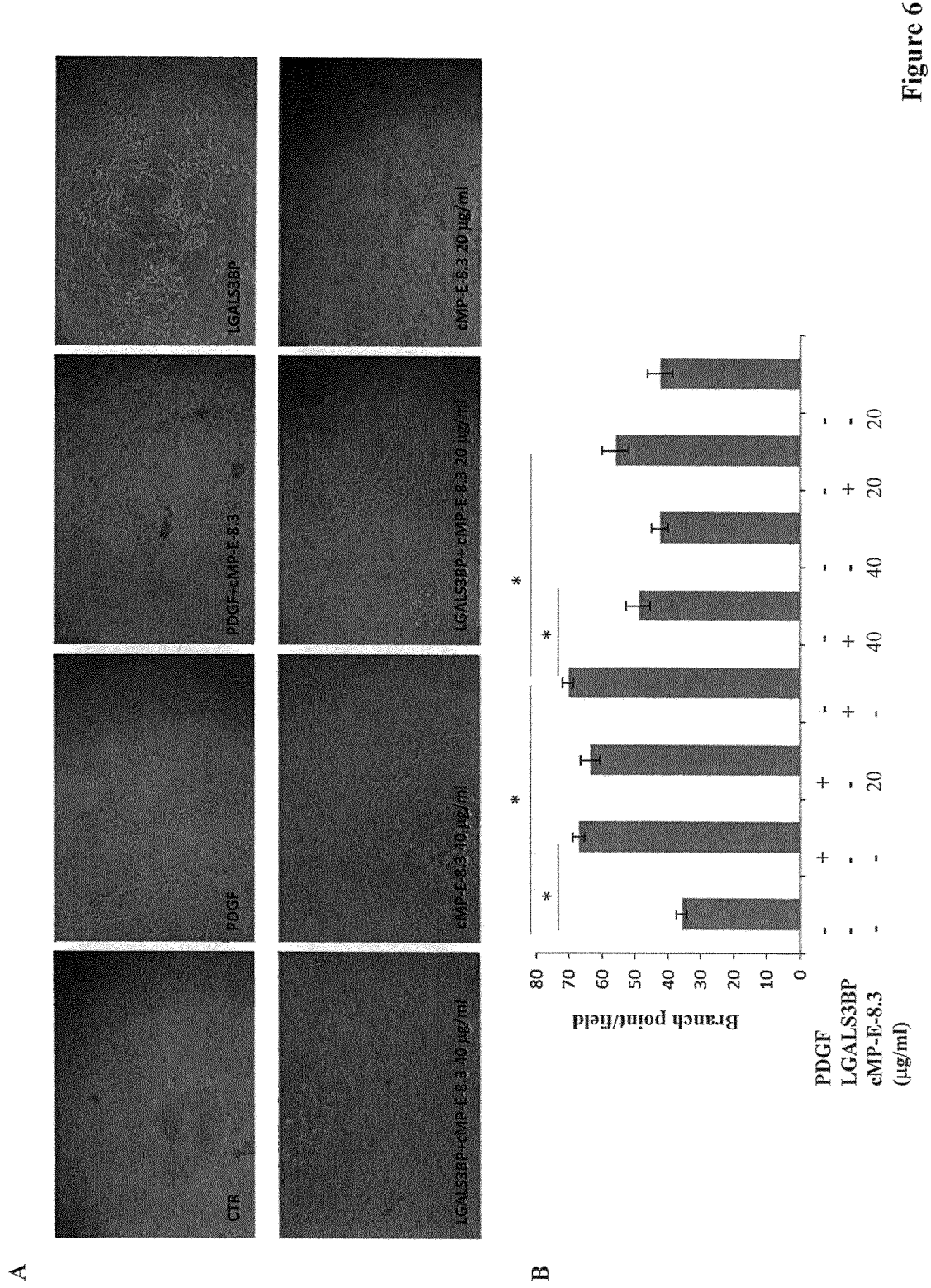
FIG. 6 shows that cMP-E-8.3 inhibits LGALS3BP-induced tube formation by pericytes on matrigel.

Materials and methods: (FIG. 6). T/G HA-VSMC human vascular smooth muscular cells were seeded at a density of $5 \times 10^4$ cells/well in F12K serum free medium. Cells were maintained in F12K serum free medium containing 10 µg/ml recombinant LGALS3BP in the absence or presence of cMP-E-8.3 at the concentrations of 20 or 40 µg/ml. PDGF (100 ng/ml) was used as a positive control. (A) Representative phase-contrast photographs of capillary-like tube formation by T/G HA-VSMC on Cultrex (Matrigel)-coated chamber slides. (B) Histograms show quantitative determination of tube formation by counting number of branch points in 4 different fields. Data are represented as mean±SEM of three independent experiments. *p<0.05.

Results: The chimeric antibody cMP-E-8.3 is able to inhibit pericyte's tube formation on matrigel induced by LGALS3BP in a dose dependent manner.

Example 8

Effect of cMP-E-8.3 on Osteosarcoma Cancer Xenografts

Figure 7:
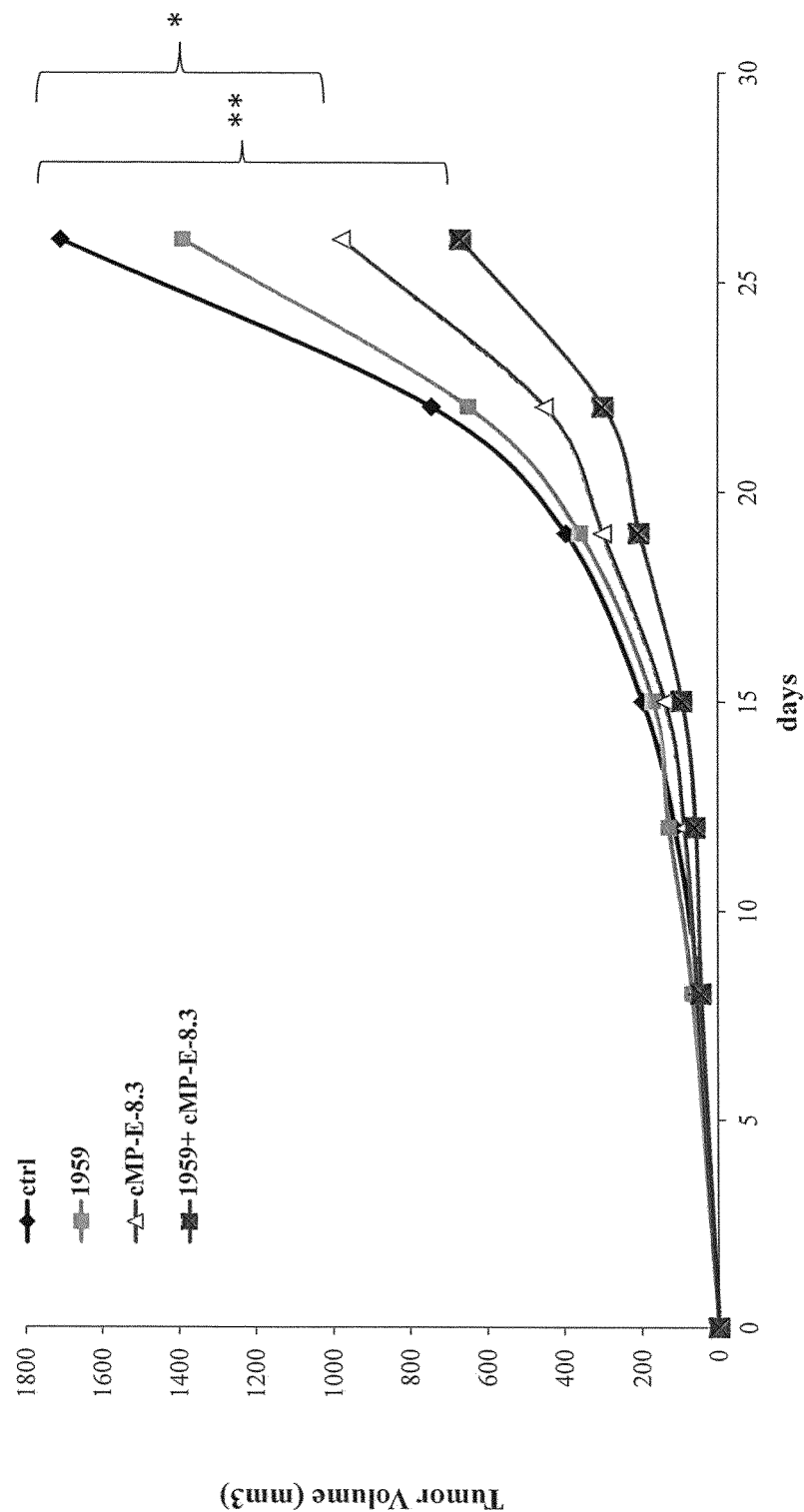
FIG. 7 shows that cMP-E-8.3 restrains growth of the human osteosarcoma Sjsa-1 xenograft in nude mice. Also, the figure shows that the inhibitory effect of cMP-E-8.3 is potentiated by 1959, a humanized antibody against the tumor secreted protein, LGALS3BP.

Materials and Methods: (FIG. 7) Human osteosarcoma cancer xenografts were established by injecting subcutaneously $5 \times 10^6$ Sjsa-1 cells in 5-week old CD1 female nude mice. Three days after cell injection, mice randomly divided into four groups of 10 animals. One group received intraperitoneal injection twice per week of 15 mg/kg of 1959 (a humanized antibody against LGALS3BP) in PBS buffer, or cMP-E-8.3 antibody at 15 mg/kg or a combination of both antibodies, each at 15 mg/kg. One group received PBS only (control group). Tumor volume was monitored two times a week by a caliper.

Results: cMP-E-8.3 treated mice show up to 40% reduction of tumor volume compared to the control mice, while the group receiving 1959 and cMP-E-8.3 show up to 70% reduction of tumor volume. *p≤0.05; **p≤0.01.

Example 9

Production and Characterization of hMP-E-8.3/ADC

Figure 9C:
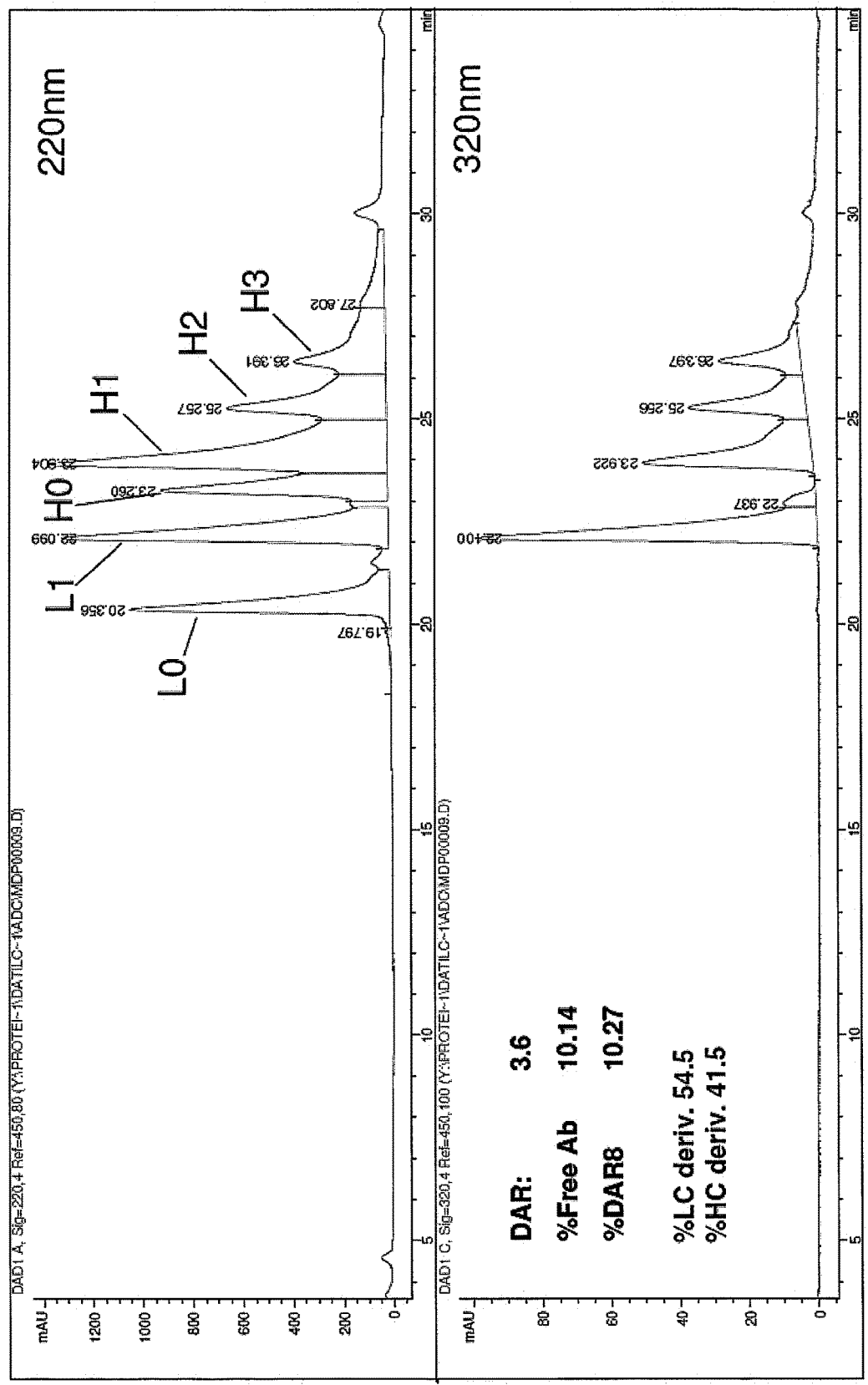
FIG. 9 shows hMP-E-8.3/ADC characterization

ADC preparation: The hMP-E-8.3/ADC was generated by partially reducing the hMP-E-8.3 antibody and conjugating the drug, a potent Minor Grove Alkylating Agent derivative of duocarmycin bearing an enzymatically cleavable linker (valine-citrulline) to the available reduced inter-chain cysteine residues. The produced hMP-E-8.3/ADC was characterized by SDS-PAGE under reducing and non reducing conditions. Three pg of naked mAb or ADC both for reducing (R) and non reducing (NR) were loaded (FIG. 9A). Size Exclusion Chromatography (SEC) was performed to determine the aggregation state. Signal was detected at two different wavelengths 220 (Blue) and 320 nm (Red) to monitor antibody and drug, respectively (FIG. 9B). Hydrophobic interaction chromatography (HIC) was performed to evaluate the presence of differently loaded isoforms in native conditions; PLRP LC/MS in reducing conditions was performed to determine the Drug Antibody Ratio (DAR). Results: No antibody degradation or aggregation was detected in the tested preparation (FIGS. 9A and B). The calculated DAR was 3.6 (FIG. 9C).

Example 10 hMP-E-8.3/ADC is Internalized by SjSA-1 Cells

Figure 10:
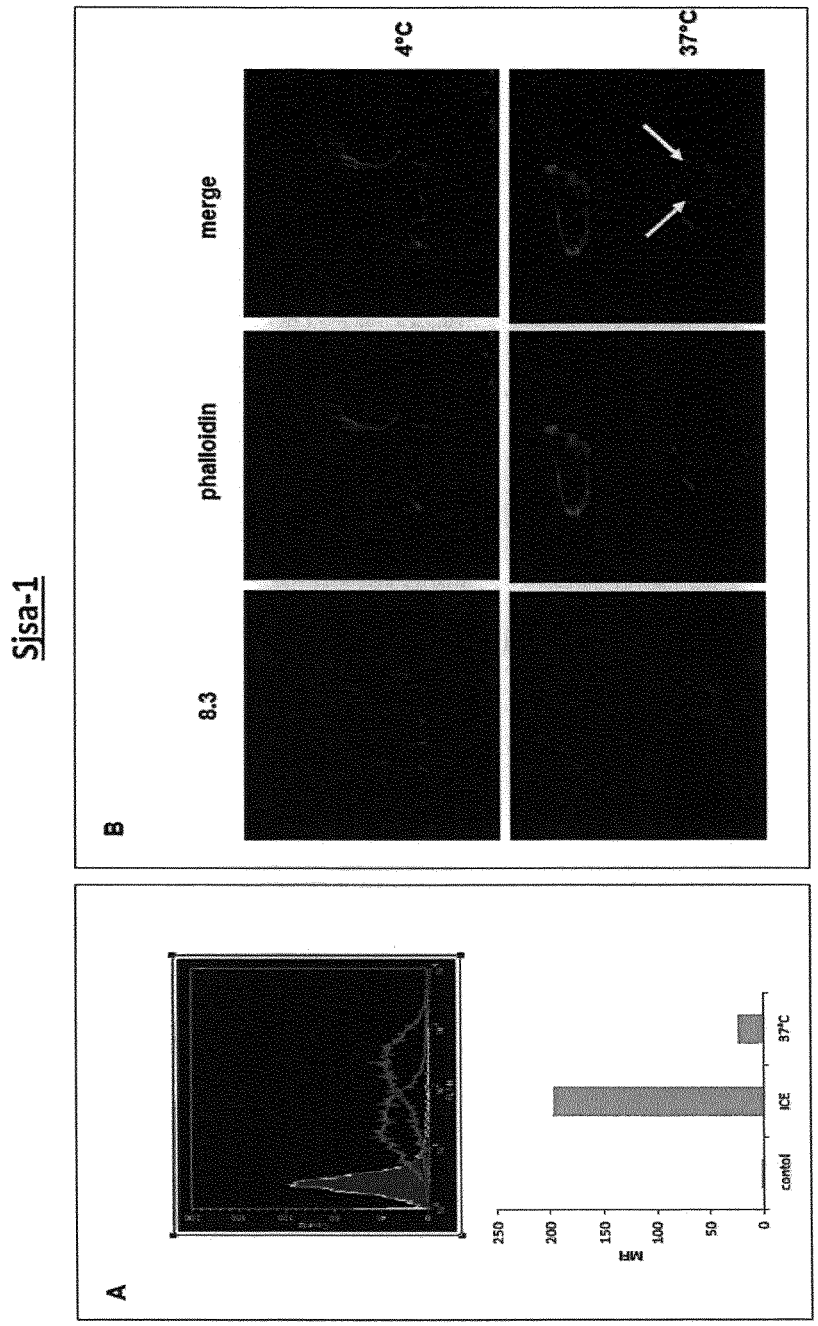
FIG. 10 shows hMP-E-8.3/ADC internalization in Sjsa-1 Endosialin positive cells by flow cytometer (2A) and by laser scanning confocal microscopy (2B).

Materials and Methods: (FIG. 10) Sjsa-1 cells were plated in 12 well-plates and grown in 10% FBS RPMI-1640 for 24 hours. Cells were then incubated with 10 µg/ml of hMP-E-8.3/ADC, for 30 minutes on ice and returned at 37° C. for 6 hours. (A) After 2 hours, cells were stained with a goat anti-human Alexa 488-conjugated secondary antibody and analysed by FACS. (B) After 2 hours, cells were fixed in 4% paraformaldehyde, permeabilized with 0.2% Triton-X100 in PBS and then stained with a fluorescein-labeled goat anti-human antibody (green staining). Cell cytoplasm was counterstained in red using Alexa Fluor phalloidin. The white arrows indicate antibody localization in the cytoplasm in cells returned at 37° C.

Results: (A) Sjsa-1 cells show goat anti human membrane positivity after 30 minutes of mMP-E-8.3 incubation on ice indicating that the antibody is completely localized on the plasma membrane. After 2 hours at 37° C., the goat anti-human signals is reduced by 80% indicating that hMP-E-8.3 has been internalized by cells. (B) Sjsa-1 cells show goat anti-human membrane positivity after 30 minutes of hMP-E-8.3 incubation on ice indicating that the antibody is completely localized on the plasma membrane. After 2 hours at 37° C., the goat anti human signals present inside the cells, in particular in the peri-nuclear region (white arrows).

Example 11 hMP-E-8.3/ADC In Vitro Antitumor Activity Correlates With Endosialin Surface Expression Level Materials and Methods: Human osteosarcoma cancer (SjSa-1), Ewing's sarcoma (A673), neuroblastoma (SK-NAS) and melanoma (A375) cells were plated in 24 wells ($1 \times 10^3$ per well) and growth in media supplemented with 10% serum in the presence or not of increasing amount of hMP-E-8.3/ADC (0.03 to 1.6 µg/ml). After 144 hrs from the beginning of treatment cells were harvested and processed for MTT staining. Results are shown as % of control (PBS treated cells).

Figure 11:
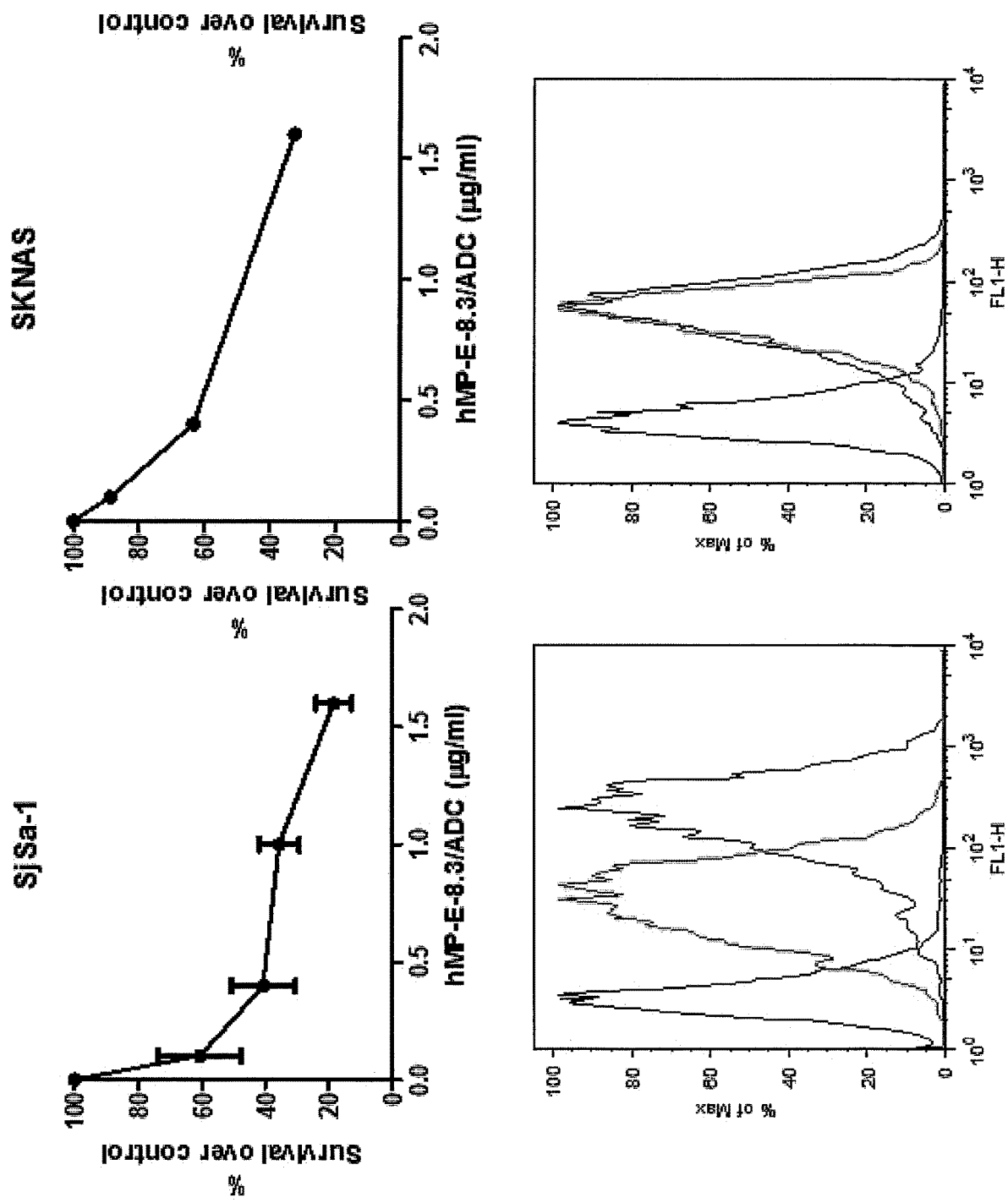
FIG. 11 shows the correlation of hMP-E-8.3/ADC in vitro antitumor activity and Endosialin surface expression
Figure 11:
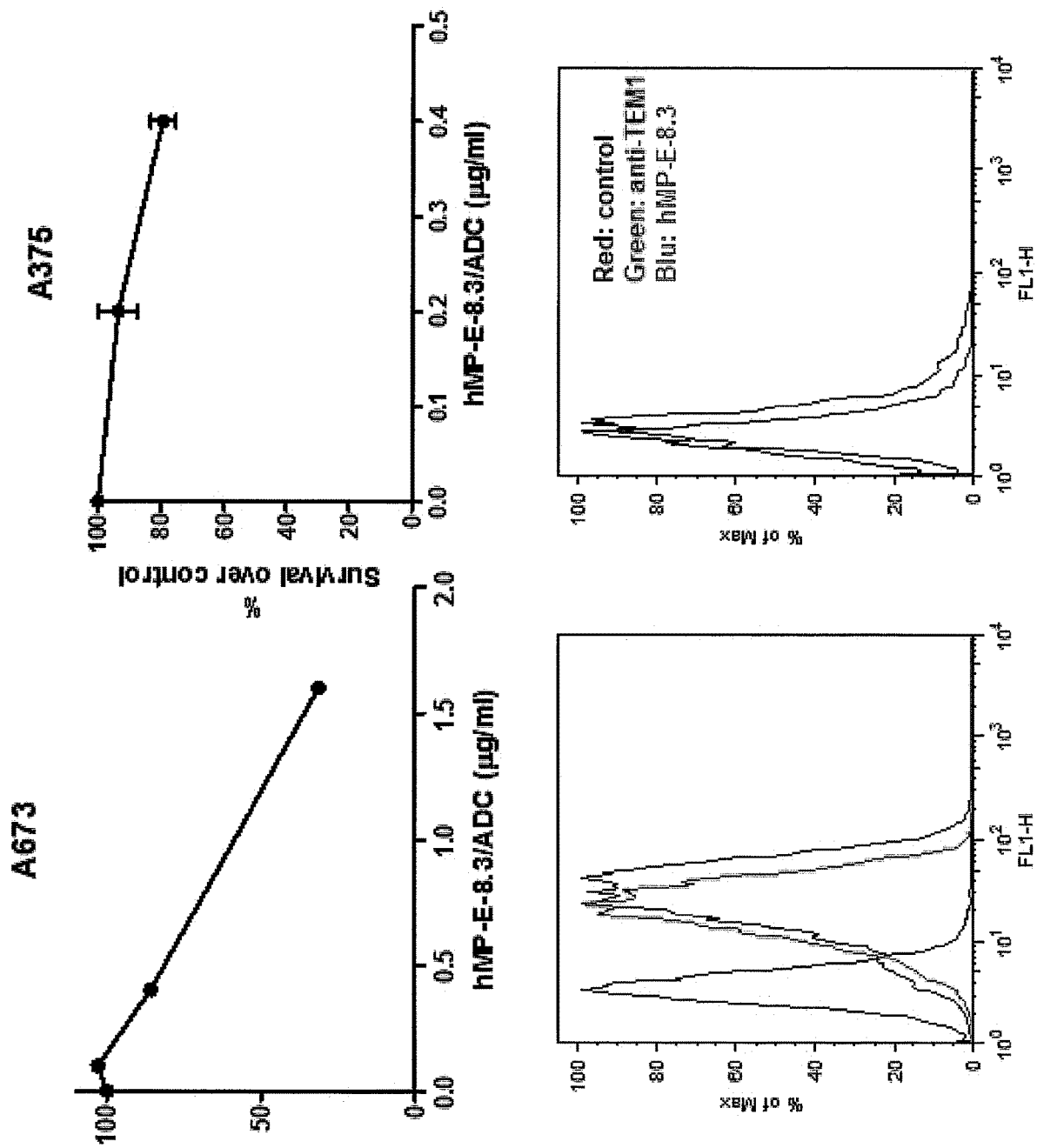

Results: hMP-E-8.3/ADC shows a strong and dose-dependent ability to inhibit cell growth. Moreover, this in vitro antitumor activity of hMP-E-8.3/ADC correlates with the amount of Endosialin receptor expression on cell surface (FIG. 11).

Example 12 hMP-E-8.3/DC54 Activity is Nearly Lost in Endosialin Knocked Down SjSa-1 Cells

Materials and Methods: TEM-1 expression was ablated in SJSA-1 cells by means of CRISPR-Cas9 system of genome editing, in accordance with the protocol developed by Zhang and co-workers[33]. After transient transfection Endosialin not-expressing cells were sorted by FACS and single cell clones isolated and propagated. Using FACS and WB clones were analyzed for Endosilain expression. Clone #3 resulted with a complete knock down for Endosialin expression. Gene destruction of both alleles was confirmed by genomic DNA sequencing.

Figure 12:
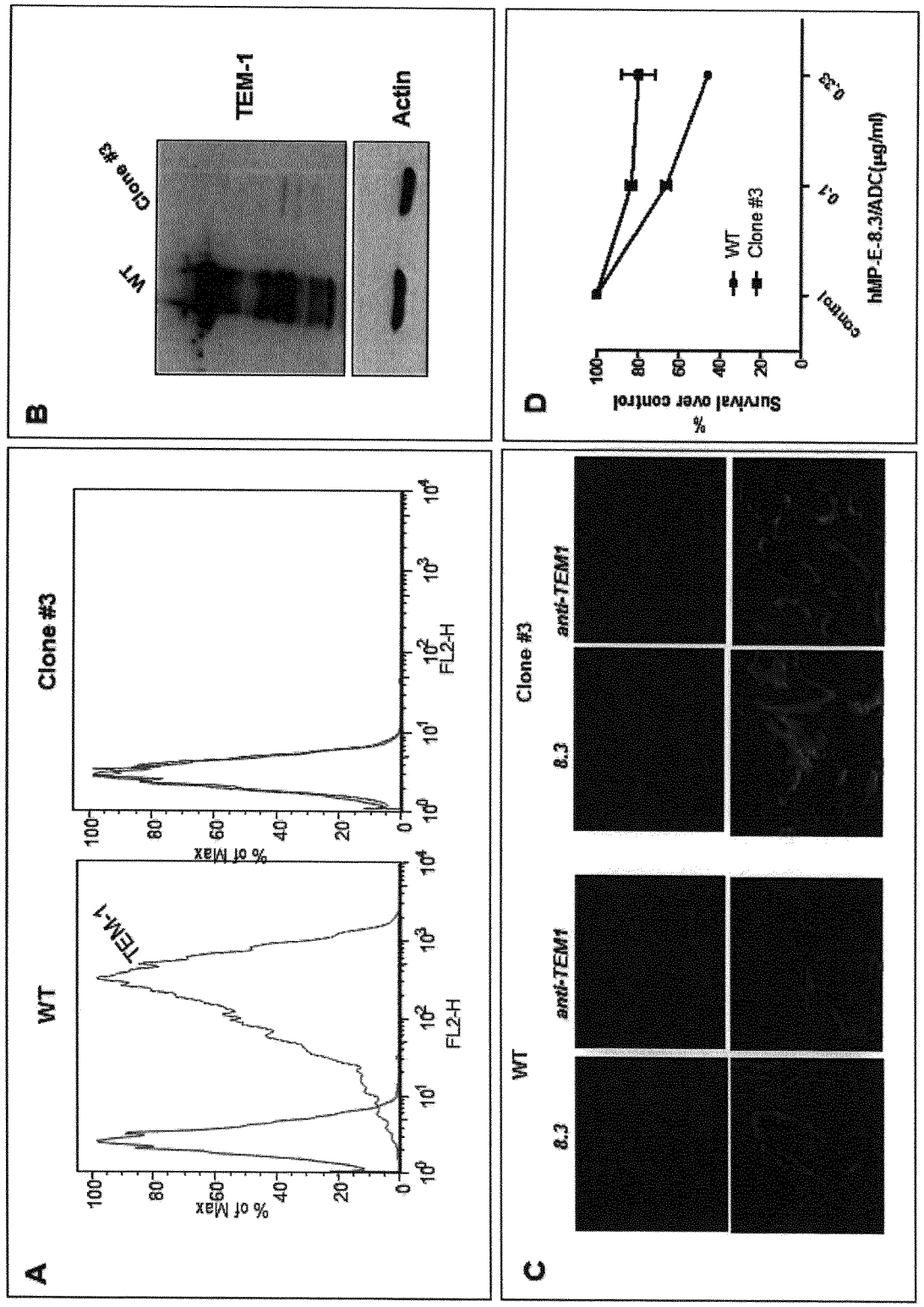
FIG. 12 shows hMP-E-8.3/ADC in vitro antitumor activity is lost/reduced in SjSa cells knocked down for Endosialin surface expression by CRISPR/Cas9 technology.

Results: loss of Endosialin expression on surface of SjSa-1 cells dramatically reduced hMP-E-8.3/ADC killing activity, indicating that ADC efficacy is target-dependent (FIG. 12)

Example 13 hMP-E-8.3/ADC Shows a Potent and Durable Antitumor Activity in Human Osteosarcoma Cancer (SjSa-1) Cenograft Materials and Methods: Human osteosarcoma cancer xenografts were established by injecting subcutaneously $2.5 \times 10^6$ Sjsa-1 cells in 5-week old CD1 female nude mice. Once tumor become palpable (Tumor Volume range 100 mm$^3$), mice were randomly divided into two groups of 6 animals. One group received intravenous injection once/weekly for two weeks of 10 mg/kg of hMP-E-8.3/ADC in PBS buffer, whereas the control group received PBS only. Tumor volume was monitored every week by a caliper. For Kaplan Meier survival curve the cut-off value for this study was volume of 1500 mm$^3$.

Results: hMP-E-8.3/ADC treated mice show a significant and durable reduction of tumor growth. Moreover, two complete remission were observed in treated mice up to 100 days form starting of treatment. Kaplan Mayer survival curve demonstrate a significant increase of survival in hMP-E-8.3/ADC treated mice (Log-rank (Mantel-Cox) Test p=0.02) (FIG. 12). Of note, hMP-E-8.3/ADC at the dosage used in this study resulted well tolerated by the animals, as no toxicity was observed in terms of weight loss.

Example 14 hMP-E-8.3/ADC Shows Superior Antitumor Activity Over the Naked Antibody in Human Osteosarcoma Cancer (SjSa-1) Xenograft Materials and Methods: Human osteosarcoma cancer xenografts were established by injecting subcutaneously $2.5 \times 10^6$ Sjsa-1 cells in 5-week old CD1 female nude mice. Once tumor become palpable (Tumor Volume range 100 mm$^3$), mice were randomly divided into three groups of 6 animals. One group received intravenous injection twice/weekly for two weeks of 10 mg/kg of hMP-E-8.3/ADC or naked hMP-E-8.3 antibody in PBS buffer, whereas the control group received PBS only. Tumor volume was monitored every week by a caliper. For Kaplan Meier survival curve the cut-off value for this study was volume of 1500 mm$^3$.

Figure 13:
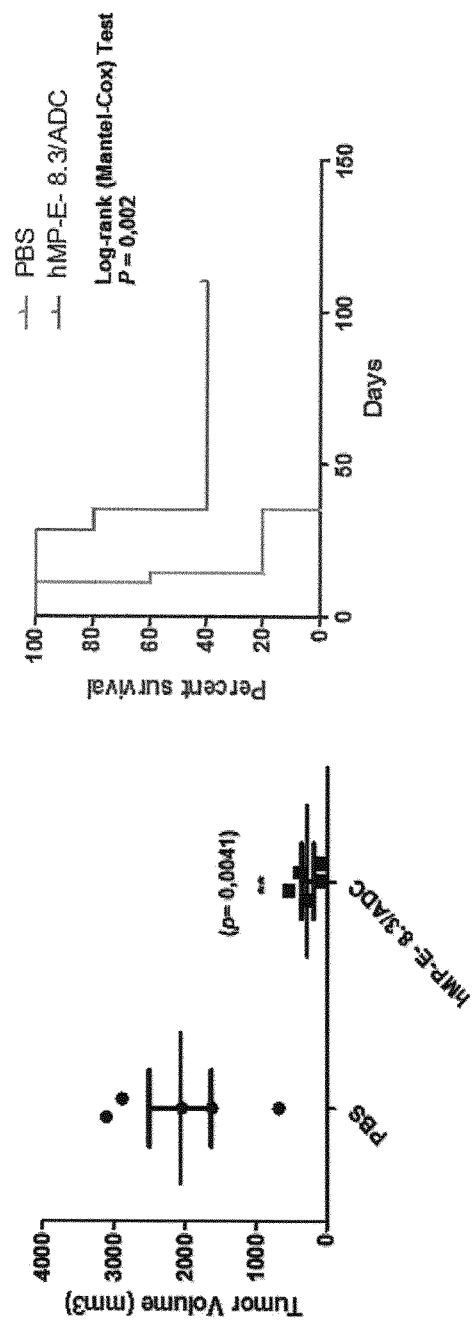
FIG. 13 shows hMP-E-8.3/ADC in vivo antitumor activity in SjSA-1 cells.
Figure 14:
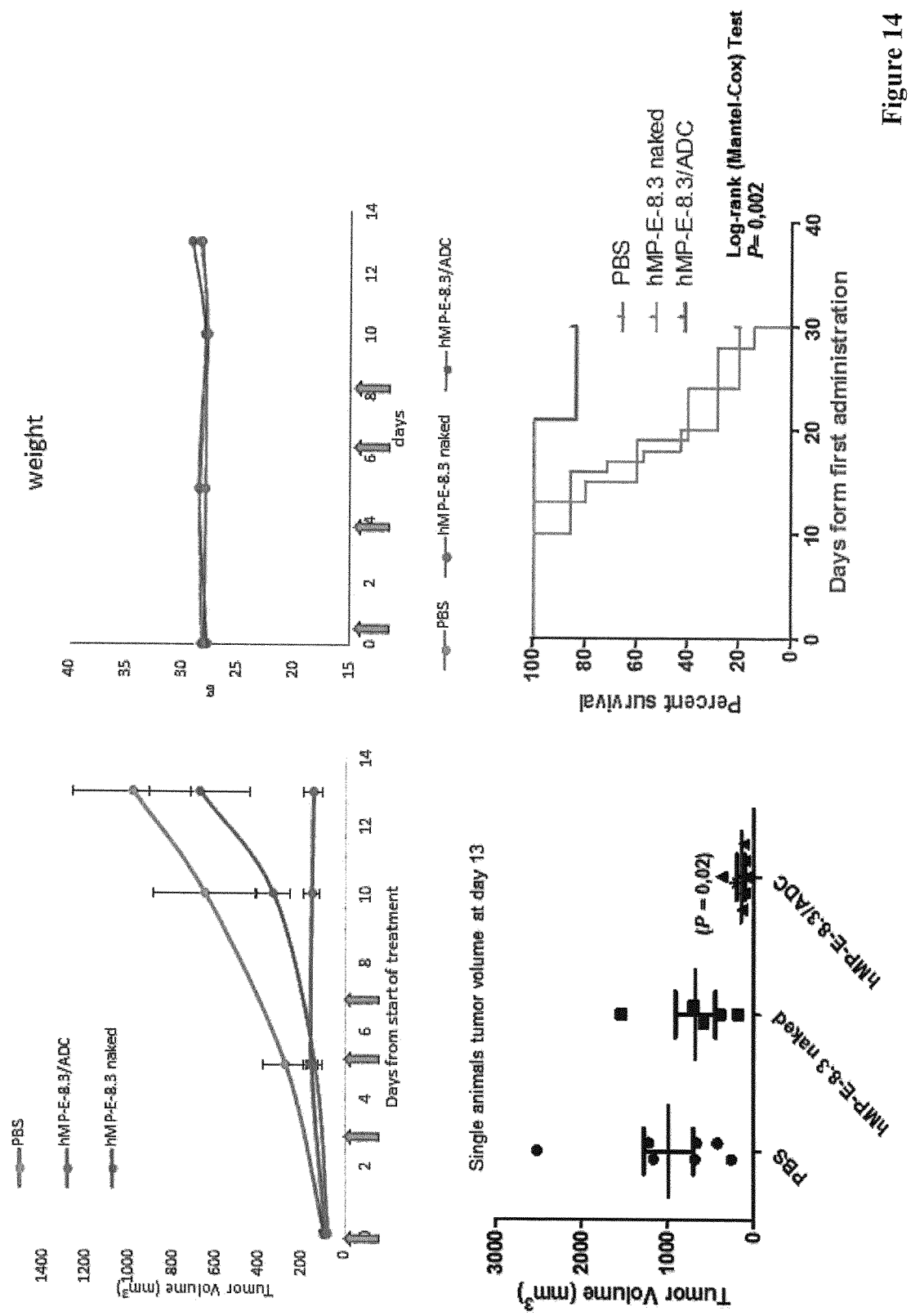
FIG. 14 shows that hMP-E-8.3/ADC in vivo antitumor activity is superior to the naked antibody in SjSA-1 cells.

Results: The naked antibody slightly reduced tumor growth, although the reduction in tumor size was not statistically significant. On the other hand, a significant and durable tumor growth inhibition was observed in mice treated with the ADC, demonstrating that the cytotoxic compound confers a far superior antitumor activity to the hMP-8.3 mAb (FIG. 13). Kaplan Mayer survival curve demonstrate a significant increase of survival in hMP-E-8.3/ADC treated mice (Log-rank (Mantel-Cox) Test p=0.002). Of note, hMP-E-8.3/ADC at the dosage used in this study resulted well tolerated by the animals, as no toxicity was observed in terms of weight loss.

REFERENCES

1. Bergers G, Benjamin L E. Tumorigenesis and the angiogenic switch. Nat Rev Cancer. 2003 June; 3(6): 401-10.
2. Christian S, Ahorn H, Koehler A, Eisenhaber F, Rodi H P, Garin-Chesa P, Park J E, Rettig W J, Lenter M C. J Biol Chem. 2001 Mar. 9; 276(10):7408-14. Epub 2000 Nov. 17. Molecular cloning and characterization of endosialin, a C-type lectin-like cell surface receptor of tumor endothelium.
3. Rettig W J, Garin-Chesa P, Healey J H, Su S L, Jaffe E A, Old L J. Proc Natl Acad Sci USA. 1992 Nov. 15; 89(22):10832-6. Identification of endosialin, a cell surface glycoprotein of vascular endothelial cells in human cancer.

4. Teicher B A. Int J Oncol. 2007 February; 30(2):305-12. Newer vascular targets: endosialin (review).
5. Brian Tomkowicz, Katherine Rybinski, Brian Foley, Wolfgang Ebel, Brad Kline, Eric Routhier, Philip Sass, Nicholas C. Nicolaides, Luigi Grasso, and Yuhong Zhou Proc Natl Acad Sci USA. 2007 Nov. 13; 104(46): 17965-17970. Interaction of endosialin/TEM1 with extracellular matrix proteins mediates cell adhesion and migration.
6. Renate Becker, Martin C Lenter, Tobias Vollkommer, Anja M Boos, Dennis Pfaff, Hellmut G Augustin, Sven Christian. FASEB J 2008 Aug. 19; 22(8):3059-67. Tumor stroma marker endosialin (Tem1) is a binding partner of metastasis-related protein Mac-2 BP/90K.
7. Piccolo E, Tinari N, Semeraro D, Traini S, Fichera I, Cumashi A, La Sorda R, Spinella F, Bagnato A, Lattanzio R, D'Egidio M, Di Risio A, Stampolidis P, Piantelli M, Natoli C, Ullrich A, Iacobelli S. J Mol Med (Berl). 2013 January; 91(1):83-94. LGALS3BP, lectin galactoside-binding soluble 3 binding protein, induces vascular endothelial growth factor in human breast cancer cells and promotes angiogenesis.
8. Marty C, Langer-Machova Z, Sigrist S, Schott H, Schwendener R A, Ballmer-Hofer K. Isolation and characterization of a scFv antibody specific for tumor endothelial marker 1 (TEM1), a new reagent for targeted tumor therapy. Cancer Lett. 2006; 235:298-308.
9. Zhao A, Nunez-Cruz S, Li C, Coukos G, Siegel D L, Scholler N. Rapid isolation of high-affinity human antibodies against the tumor vascular marker Endosialin/TEM1, using a paired yeast-display/secretory scFv library platform. J Immunol Methods. 2011; 363:221-232.
10. Rouleau C, Curiel M, Weber W, Smale R, Kurtzberg L, Mascarello J, Berger C, Wallar G, Bagley R, Honma N, Hasegawa K, Ishida I, Kataoka S, Thurberg B L, Mehraein K, Horten B, Miller G, Teicher B A. Endosialin protein expression and therapeutic target potential in human solid tumors: sarcoma versus carcinoma. Clin Cancer Res. 2008 Nov. 15; 14(22):7223-36.
11. Bagley R G. Endosialin: from vascular target to biomarker for human sarcomas. Biomark Med. 2009 October; 3(5):589-604.
12. Simonavicius N, Robertson D, Bax D A, Jones C, Huijbers I J, Isacke C M. Endosialin (CD248) is a marker of tumor-associated pericytes in high-grade glioma. Mod Pathol.
13. Christian S, Winkler R, Helfrich I, Boos A M, Besemfelder E, Schadendorf D, Augustin H G. Endosialin (Tem1) is a marker of tumor-associated myofibroblasts and tumor vessel-associated mural cells. The American journal of pathology. 2008; 172(2):486-494.
14. MacFadyen J R, Haworth O, Roberston D, Hardie D, Webster M T, Morris H R, Panico M, Sutton-Smith M, Dell A, van der Geer P. et al. Endosialin (TEM1, CD248) is a marker of stromal fibroblasts and is not selectively expressed on tumor endothelium. FEBS letters. 2005; 579(12):2569-2575.
15. Brady J, Neal J, Sadakar N, Gasque P. Human endosialin (tumor endothelial marker 1) is abundantly expressed in highly malignant and invasive brain tumors. Journal of neuropathology and experimental neurology. 2004; 63(12):1274-1283.
16. Davies G, Cunnick G H, Mansel R E, Mason M D, Jiang W G. Levels of expression of endothelial markers specific to tumor-associated endothelial cells and their correlation with prognosis in patients with breast cancer. Clin Exp Metastasis. 2004; 21(1):31-37.
17. 14.Maia M, DeVriese A, Janssens T, Moons M, Lories R J, Tavernier J, Conway E M. CD248 facilitates tumor growth via its cytoplasmic domain. BMC Cancer. 2011 May 8; 11:162.
18. Tomkowicz B, Rybinski K, Sebeck D, Sass P, Nicolaides N C, Grasso L, Zhou Y. Endosialin/TEM-1/CD248 regulates pericyte proliferation through PDGF receptor signaling. Cancer Biol Ther. 2010 Jun. 1; 9(11):908-15.
19. Yang J, Zhang W. New molecular insights into osteosarcoma targeted therapy. Curr Opin Oncol. 2013 July; 25(4):398-406.
20. Rouleau C, Sancho J, Campos-Rivera J, Teicher B A. Endosialin expression inside populations in human sarcoma cell lines. Oncol Lett. 2012 February; 3(2): 325-329.
21. Rouleau C, Smale R, Sancho J, Fu Y S, Kurtzberg L, Weber W, Kruger A, Jones C, Roth S, Bormann C, Dunham S, Krumbholz R, Curiel M, Wallar G, Mascarello J, Campos-Rivera J, Horten B, Schmid S, Miller G, Teicher B A. Endosialin: a novel malignant cell therapeutic target for neuroblastoma. Int J Oncol. 2011 October; 39(4):841
22. Rouleau C, Smale R, Fu Y S, Hui G, Wang F, Hutto E, Fogle R, Jones C M, Krumbholz R, Roth S, Curiel M, Ren Y, Bagley R G, Wallar G, Miller G, Schmid S, Horten B, Teicher B A. Endosialin is expressed in high grade and advanced sarcomas: evidence from clinical specimens and preclinical modeling. Int J Oncol. 2011 July; 39(1):73-89.
23. Carson-Walter E B, Winans B N, Whiteman M C, Liu Y, Jarvela S, Haapasalo H, Tyler B M, Huso D L, Johnson M D, Walter K A. Characterization of TEM1/endosialin in human and murine brain tumors. BMC Cancer. 2009 Nov. 30; 9:417.
24. A Jemal, R Siegel, E Ward et al. Cancer Statistics, 2009. CA Cancer J Clin 59: 225-49 (2009).
25. Mehlen P, Puisieux A. Metastasis: a question of life or death. Nat Rev Cancer; 6:449-58 (2006).
26. Chambers A F, Groom A C, MacDonald I C. Dissemination and growth of cancer cells in metastatic sites. Nat Rev Cancer 2:563-72 (2002).
27. Peters, C. and S. Brown, Antibody-drug conjugates as novel anti-cancer chemotherapeutics. Biosci Rep, 2015. 35(4).
28. Thomas, A., B. A. Teicher, and R. Hassan, Antibody-drug conjugates for cancer therapy. Lancet Oncol, 2016. 17(6): p. e254-62.
29. Kohler G, Milstein C. Continuous cultures of fused cells secreting antibody of predefined specificity. Nature 1975; 256:495-497.
30. Clackson T, Hoogenboom H R, Griffiths A D, Winter G. Making antibody fragments using phage display libraries. Nature 1991; 15; 352(6336):624-8.
31. Jones P T, Dear P H, Foote J, Neuberger M S, Winter G. Replacing the complementarity-determining regions in a human antibody with those from a mouse. Nature, 321:522-525 (1986).
32. Riechmann L, Clark M, Waldmann H, Winter G Reshaping human antibodies for therapy. Nature, 332: 323-327 (1988).
33. Cong L, Ran F A, Cox D, Lin S, Barretto R, Habib N, et al. Multiplex genome engineering using CRISPR/Cas systems. Science. 2013; 339:819-23.

The invention claimed is:

1. An antibody or functional fragment thereof, which is directed against an epitope between amino acids 477-488 of human Endosialin according to SEQ ID NO: 1, and which comprises:

(i) a heavy chain comprising:
- a heavy chain complementarity determining region 1 (CDRH1) having the amino acid sequence as shown in SEQ ID NO: 2,
- a heavy chain complementarity determining region 2 (CDRH2) having the amino acid sequence as shown in SEQ ID NO: 3, and
- a heavy chain complementarity determining region 3 (CDRH3) having the amino acid sequence as shown in SEQ ID NO: 4, and (ii) a light chain comprising:
- a light chain complementarity determining region 1 (CDRL1) having the amino acid sequence as shown in SEQ ID NO: 5,
- a light chain complementarity determining region 2 (CDRL2) having the amino acid sequence as shown in SEQ ID NO: 6, and
- a light chain complementarity determining region 3 (CDRL3) having the amino acid sequence as shown in SEQ ID NO: 7.

2. The antibody or functional fragment thereof of claim 1, which comprises:
- a heavy chain variable region comprising an amino acid sequence as shown in SEQ ID NO: 8 or an amino acid sequence having a sequence identity of at least 90% thereto, and a light chain variable region comprising an amino acid sequence as shown in SEQ ID NO: 9 or an amino acid sequence having a sequence identity of at least 90% thereto.

3. The antibody or functional fragment thereof of claim 1, which is a Fab fragment, a Fab' fragment, a F(ab')$_2$ fragment, a Fv-fragment, a diabody, a scFv, a small modular immunopharmaceutical (SMIP), or a single chain antibody.

4. The antibody or functional fragment thereof of claim 1, which is an IgG1-, IgG2-, IgG3- or IgG4-type antibody or an IgM-, IgA1-, IgA2-, IgAsec-, IgD- or IgE-type antibody, or a fragment thereof.

5. The antibody or functional fragment thereof of claim 1, which is a monoclonal antibody, a humanized antibody, a chimeric antibody, or a multispecific antibody, or a fragment thereof.

6. The antibody or functional fragment thereof of claim 1, which comprises:
   a heavy chain variable region comprising an amino acid sequence as shown in SEQ ID NO: 18, SEQ ID NO: 19, SEQ ID NO: 20, or SEQ ID NO: 21 or an amino acid sequence having a sequence identity of at least 90% thereto, and
   a light chain variable region comprising an amino acid sequence as shown in SEQ ID NO: 22, SEQ ID NO: 23, SEQ ID NO: 24, or SEQ ID NO: 25 or an amino acid sequence having a sequence identity of at least 90% thereto.

7. The antibody or functional fragment thereof of claim 1, wherein the antibody or functional fragment thereof is linked to a labeling group, an effector group, or a therapeutic group.

8. The antibody or functional fragment thereof of claim 7, wherein the antibody or functional fragment thereof is linked to a paramagnetic, radioactive or fluorogenic ion that is detectable via imaging techniques.

9. The antibody or functional fragment thereof of claim 7, wherein the antibody or functional fragment thereof is linked to an anticellular agent that is an anti-mitotic or DNA damaging agent capable of killing or suppressing the growth or cell division of endothelial cells.

10. The antibody or functional fragment thereof of claim 9, wherein the anticellular agent comprises a chemotherapeutic agent, radioisotope or cytotoxin.

11. The antibody or functional fragment thereof of claim 10, wherein the anticellular agent comprises an antimetabolite, an anthracycline, a *vinca* alkaloid, an antibiotic, an alkylating agent or a plant-, fungus- or bacteria-derived toxin.

12. The antibody or functional fragment thereof of claim 9, wherein the anticellular agent comprises a DNA damaging agent that is a Minor Grove Binder duocarmycin derivative.

13. The antibody or functional fragment thereof of claim 10, wherein the cytotoxin comprises an A chain toxin, a ribosome inactivating protein, a-sarcin, aspergillin, restrictocin, a ribonuclease, diphtheria toxin or *Pseudomonas* exotoxin.

14. The antibody or functional fragment thereof of claim 10, wherein the cytotoxin comprises deglycosylated ricin A chain.

15. The antibody or functional fragment thereof of claim 1, wherein the antibody or functional fragment thereof recognizes human Endosialin that is expressed on the cell surfaces of tumor vascular cells to a greater degree than on the surfaces of normal endothelial cells.

16. The antibody or functional fragment thereof of claim 1, wherein the antibody or functional fragment thereof is a bispecific antibody that recognizes the human tumor-associated antigen LGALS3BP.

17. A pharmaceutical composition comprising an antibody or functional fragment thereof of claim 1.

18. The pharmaceutical composition according to claim 17, further comprising an active agent.

19. The pharmaceutical composition of claim 17, further comprising a pharmaceutically acceptable carrier, diluent, or excipient.

20. The antibody or functional fragment thereof of claim 1, which is a murine antibody, or a fragment thereof.

21. The antibody or functional fragment thereof of claim 1, which is a bispecific antibody, or a fragment thereof.

22. The pharmaceutical composition of claim 17, further comprising an active agent that is an antibody.

23. The pharmaceutical composition of claim 17, further comprising an active agent that is an antibody fragment.

24. The pharmaceutical composition of claim 17, further comprising an active agent that is an anti-neoplastic agent selected from the group consisting of antibodies, small molecules, antimetabolites, alkylating agents, topoisomerase inhibitors, microtubule-targeting agents, kinase inhibitors, protein synthesis inhibitors, immuno-therapeutics, and hormones or analogs thereof.

* * * * *